(12) United States Patent
Hausheer

(10) Patent No.: US 7,687,487 B2
(45) Date of Patent: Mar. 30, 2010

(54) CAMPTOTHECIN-ANALOG WITH A NOVEL, "FLIPPED" LACTONE-STABLE, E-RING AND METHODS FOR MAKING AND USING SAME

(75) Inventor: Frederick H. Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 11/788,223

(22) Filed: Apr. 19, 2007

(65) Prior Publication Data

US 2008/0261919 A1  Oct. 23, 2008

(51) Int. Cl.
*A61K 31/33* (2006.01)
*C07D 491/22* (2006.01)

(52) U.S. Cl. .......................................... 514/183; 546/48
(58) Field of Classification Search ........................ None
See application file for complete search history.

(56) References Cited

OTHER PUBLICATIONS

Jordan, V. C. 'Tamoxifen: a most unlikely pioneering medicine' Nature Reviews: Drug Discovery, 2, p. 205-213, 2003.*
Dorwald, F. Zaragoza. Side Reactions in Organic Synthesis: A Guide to Successful Synthesis Design Weinheim: WILEY-VCH Verlag GmbH & Co. KGaA, Preface, p. ix, 2005.*

\* cited by examiner

*Primary Examiner*—Brandon J Fetterolf
*Assistant Examiner*—Christopher R Stone
(74) *Attorney, Agent, or Firm*—Scott A. Whitaker

(57) ABSTRACT

The present invention discloses: (i) a novel, lactone-stable, "flipped" E-ring camptothecin, pharmaceutically-acceptable salts, and/or analogs thereof; (ii) methods of synthesis of said novel, lactone-stable, "flipped" E-ring camptothecin, pharmaceutically-acceptable salts, and/or analogs thereof; (iii) pharmaceutically-acceptable formulations comprising said novel, lactone-stable, "flipped" E-ring camptothecin, pharmaceutically-acceptable salts, and/or analogs thereof, and, optionally, one or more additional chemotherapeutic agents; (iv) methods of administration of said novel, lactone-stable, "flipped" E-ring camptothecin, pharmaceutically-acceptable salts, and/or analogs thereof, and, optionally, one or more additional chemotherapeutic agents, to subjects in need thereof; and (v) devices for the administration of said novel, lactone-stable, "flipped" E-ring camptothecin, pharmaceutically-acceptable salts, and/or analogs thereof, and, optionally, one or more chemotherapeutic agents, to subjects in need thereof.

3 Claims, No Drawings

CAMPTOTHECIN-ANALOG WITH A NOVEL, "FLIPPED" LACTONE-STABLE, E-RING AND METHODS FOR MAKING AND USING SAME

FIELD OF THE INVENTION

The present invention relates to: (i) a novel, lactone-stable, "flipped" E-ring camptothecin, pharmaceutically-acceptable salts, and/or analogs thereof; (ii) methods of synthesis of said novel, lactone-stable, "flipped" E-ring camptothecin, pharmaceutically-acceptable salts, and/or analogs thereof; (iii) pharmaceutically-acceptable formulations comprising said novel, lactone-stable, "flipped" E-ring camptothecin, pharmaceutically-acceptable salts, and/or analogs thereof, and, optionally, one or more additional chemotherapeutic agents; (iv) methods of administration of said novel, lactone-stable, "flipped" E-ring camptothecin, pharmaceutically-acceptable salts, and/or analogs thereof, and, optionally, one or more additional chemotherapeutic agents, to subjects in need thereof; and (v) devices for the administration of said novel, lactone-stable, "flipped" E-ring camptothecin, pharmaceutically-acceptable salts, and/or analogs thereof, and, optionally, one or more chemotherapeutic agents, to subjects in need thereof.

BACKGROUND OF THE INVENTION

I. Camptothecin (CPT) and Initial Clinical Trials

Camptothecin (CPT; IUPAC Nomenclature: (S)-4-Ethyl-4-hydroxy-1 H-pyrano[3',4':6,7]indolizino[1,2-b]quinoline-3,14(4H,12H)-dione) and certain of its analogs have been shown to possess varying degrees of anti-neoplastic activity. Presently, two CPT analogs (Irinotecan™ and Topotecan™, as discussed below) have been approved for therapeutic use in the United States by the Food and Drug Administration (FDA) for various forms of solid neoplasms.

CPT was initially isolated in 1966 by Wall, et al., from *Camptotheca accuminata*, (Nyssaceae family) a Chinese yew. See, Wall, M. E., et al., Plant chemotherapeutic agents. I. The Isolation and Structure of Camptothecin, a Novel Alkaloidal Leukemia and Tumor Inhibitor from *Camptotheca Acuminata*. *J. Am. Chem. Soc.* 88:3888-3890 (1966)).

The structure of this originally isolated camptothecin (CPT) is shown below:

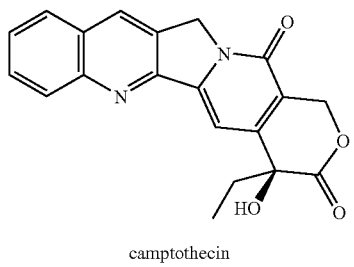

camptothecin

By the early 1970's, CPT had reached Phase I and Phase II clinical trials and although it was found to possess anti-tumor activity, there were numerous deleterious physiological side-effects associated with its use. The side-effects included, but were not limited to, severe and unpredictable myelosuppression, gastrointestinal toxicity, hemorrhagic cystitis, alopecia, diarrhea, nausea, vomiting and the like. These toxicities, found during early clinical studies, rendered the drug "unmanageable" during this time period. See, Muggia, F. M.; et al., Phase I Clinical Trial of Weekly and Daily Treatment With Camptothecin (NSC-100880): Correlation With Preclinical Studies. *Cancer Chemother. Rep.* 56:515-521 (1972); Schaeppi, U., et al., Toxicity of Camptothecin (NSC-100880). *Cancer Chemother. Rep.* 5:25-36 (1974).

In order to demonstrate both the utility and novelty of the present invention, it will be instructive to engage in brief review of the published literature dealing with human clinical trials conducted with administered in a parenteral manner. Physicochemical studies of CPT found that the closed E-ring lactone form of CPT possessed extremely poor solubility in water (i.e., approximately 0.1 µg of drug dissolving in 1 mL of water). In addition, of the two CPT enantiomers, the naturally occurring (S)-isomer was found to be more potent than the (R)-isomer. See, e.g., Motwani, M. V., et al., Flavopiridol (Flavo) Potentiates the SN-38-Induced Apoptosis in Association with Downregulation of Cyclin Dependent Kinase Inhibitor p21waf1/cip1 in HCT116 Cells. *Proc. Am. Assoc. Cancer Res.* 41:32-43 (2000). These different properties of the various analogs are caused by the different chemical substituents on the core structure of CPT.

Thus, because of its extremely poor water solubility, in order for CPT to be administered in human clinical trials, it was initially formulated using sodium hydroxide. It is important to note, that all of these early clinical studies used sodium hydroxide formulations of CPT in order to markedly increase the water solubility (i.e., hydrophilicity) of the molecule to allow sufficient quantities of the agent to be administered parenterally to patients. The sodium hydroxide formulation of CPT created more water soluble CPT species that permitted clinicians to administer larger concentrations of CPT with smaller medication volumes of administration, thereby allowing sufficiently higher doses of the drug to be administered to cancer subjects undergoing Phase I and Phase II clinical trials. However, it was subsequently established that this formulation resulted in hydrolysis of the lactone E-ring of the camptothecin molecule, thus forming the water soluble carboxylate form of CPT which only possessed approximately one-tenth or less of the anti-tumor potency of the original, non-hydrolyzed lactone form of CPT. The clinical trials performed using the sodium hydroxide-formulated CPT provide to be highly disappointing, due to both the frequently-observed significant systemic toxicities and the lack of anti-neoplastic activity. It was subsequently ascertained that the drug's relative low hydrophilicity, was the most important reason for these side-effects. This low aqueous solubility of CPT in the lactone form greatly limited the practical clinical utility of the drug because prohibitively large volumes of fluid had to be administered to the subject in order to provide an effective dose of the drug. Because of the potent anti-neoplastic activity and poor water solubility of CPT lactone forms and many of its analogs in water, a great deal of effort was directed at generating new CPT lactone analogs that possessed greater aqueous solubility. Water soluble CPT analogs should not exist in large amounts in the open E-ring form but, alternately, should predominantly remain in the closed-ring lactone form, in order to be active. Thus, CPT analogs where equilibrium favors the closed-ring lactone form are desirable for administration.

II. Pharmacological Activity of CPT

Despite these earlier disappointing side-effects, increasing clinical interest in CPT was evoked during the 1980s, as a result of the revelation of its mechanism of action (i.e., Topoisomerase I inhibition). This new information regarding the mechanism of action of CPT analogs served to rekindle the interest in developing new Topo I inhibitors for use as anti-neoplastic drugs and subsequently several research groups began attempting to develop new CPT analogs for cancer therapy. See, Hsiang, Y. H., et al., Camptothecin Induces Protein-Linked DNA Breaks Via Mammalian DNA Topoisomerase I. *J. Biol. Chem.* 260:14873-14878 (1985); Hsiang, Y. H.; Liu, L. F., Identification of Mammalian DNA Topoisomerase I as an Intracellular Target of the Anticancer Drug Camptothecin. *Cancer Res.* 48:1722-1726 (1988); Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989).

Several clinically important anticancer drugs kill tumor cells by affecting DNA Topoisomerases. Topoisomerases are essential nuclear enzymes that function in DNA replication and tertiary structural modifications (e.g., overwinding, underwinding, and catenation) which normally arise during replication, transcription, and perhaps other DNA processes. Two major Topoisomerases that are ubiquitous to all eukaryotic cells: (i) Topoisomerase I (Topo I) which cleaves single stranded DNA and (ii) Topoisomerase II (Topo II) which cleaves double stranded DNA. Topoisomerase I is involved in DNA replication; it relieves the torsional strain introduced ahead of the moving replication fork.

Topoisomerase I (Topo I) is a monomeric 100 kDal polypeptide containing 765 amino acids, and is encoded by a gene located on chromosome 20q12-13.2. See, e.g., Creemers, G. J., et al., Topoisomerase I Inhibitors: Topotecan and Irinotecan. *Cancer Treat. Rev.* 20:73-96 (1994); Takimoto, C. H.; Arbuck, S. G. The Camptothecins. *Cancer Chemother and Biother. 2nd edition* (B. L. Chabner, D. L. Longo (eds)), 463-384 (1996). It is an essential enzyme in DNA replication and RNA transcription, and is present in all eukaryotic (including tumor) cells. Since normal DNA is super-coiled, and tightly fitted in the chromosomes, the DNA-replication fork is unable to synthesize new DNA out of this topological constrained DNA. Topo I acts in an ATP-independent fashion, by binding to super-coiled DNA and cleaving a phosphodiester bond, resulting in a single-strand break. At the same time, Topo I forms a covalent reversible adduct between a tyrosine residue at position 723 of Topo I and the 3' end of the single-strand DNA molecule, called the cleavable complex. The DNA molecule is able to rotate freely around the intact single DNA strand, and relaxation of the DNA occurs. After the religation of the cleavage, Topo I dissociates from the DNA. The cleavable complex usually is present for only a short time, just to allow the single uncleaved DNA strand to unwind.

Specifically, it was found that CPT forms a reversible covalent complex comprising: Topo I-CPT-DNA. In brief, the primary mechanism of action of CPT is the inhibition of Topo I by blocking the rejoining step of the cleavage/relegation reaction of Topo I, thus resulting in the accumulation of covalent reaction intermediates (i.e., the cleavable complex). CPT-based cellular apoptosis is S-phase-specific killing through potentially lethal collisions between advancing replication forks and Topo I DNA complexes. Two repair responses to Topo I-mediated DNA damage involving covalent modification of Topo I have been identified. The first involves activation of the Ubiquitin/26S proteasome pathway, leading to degradation of Topo I (CPT-induced Topo I down-regulation). The second involves the Small Ubiquitin-like Modifier (SUMO) conjugation to Topo I. These repair mechanisms for Topo I-mediated DNA damage play an important role in determining CPT sensitivity/resistance in tumor cells.

Topo I purified from human colon carcinoma cells or calf thymus has been shown to be inhibited by CPT. CPT, Irinotecan™ (CPT-11) and an additional Topo I inhibitor, Topotecan, has been in used in clinical trials to treat certain types of human cancer. For the purpose of this invention, CPT analogs include: 7-ethyl-10-[4-(1-piperidino)-1-piperidino]carbonyloxy camptothecin (Irinotecan™ or CPT-11), 10-hydroxy-7-ethyl camptothecin (HECPT), 9-aminocamptothecin, 10,11 methylenedioxy camptothecin and 9-dimethylaminomethyl-10-hydroxy camptothecin (Topotecan). These CPT analogs use the same mechanism to inhibit Topo I; they stabilize the covalent complex of enzyme and strand-cleaved DNA, which is an intermediate in the catalytic mechanism. These analogs have no binding affinity for either isolated DNA or Topo I but do bind with measurable affinity to the enzyme-DNA complex. The stabilization of the Topo I "cleavable complex" by CPT and analogs is readily reversible.

Topoisomerase II (Topo II) works in a similar way to Topo I, with the difference being that the former enzyme acts ATP-dependently, to cause reversible doublestrand DNA cleavage, in the relaxation of DNA. Direct interference of CPTs with Topo II has not been described. However, it has been reported that Irinotecan™ (CPT-11) treatment sensitizes some tumor-xenografts in mice to Topo II inhibitors, by increasing the Topo II mRNA expression after 24 and 48 hours. This suggests that combination therapies with Topo I and Topo II targeting chemotherapy for human solid tumors might be valuable. The CPT analogs inhibit the religation reaction of Topo I by selectively inducing a stabilization of the cleavable complexes at Topo I sites bearing a guanine residue at the 5'-terminus of the enzyme mediated breaks. See, e.g., Svejstrup, J. Q., et al., Technique for Uncoupling the Cleavage and Religation Reactions of Eukaryotic Topoisomerase I. The Mode of Action of Camptothecin at a Specific Recognition Site. *J. Mol. Biol.* 222:669-678 (1991); Jaxel, C., et al., Effect of Local DNA Sequence on Topoisomerase I Cleavage in the Presence or Absence of Camptothecin. *J. Biol. Chem.* 266: 20418-20423 (1991); Tanizawa, A., et al., Induction of Cleavage in Topoisomerase I c-DNA by Topoisomerase I Enzymes From Calf Thymus and Wheat Germ in the Presence and Absence of Camptothecin. *Nucl. Acids Res.* 21:5157-5166 (1994). Although this stabilization in itself is reversible, an irreversible doublestrand break occurs when a replication fork meets a cleavable complex. The higher the levels of Topo I, the higher the frequency of cleavable complexes, and the higher the number of DNA breaks. These breaks may lead to cell cycle arrest in the S/G2-phase, activation of apoptosis pathways, and finally to cell death. See, e.g., Hsiang, Y. H., et al., Arrest of Replication Forks by Drug-Stabilized Topoisomerase I DNA Cleavable Complexes as a Mechanism of Cell Killing by Camptothecin. *Cancer Res.* 49:5077-5082 (1989). As a result of this, Topo I inhibitors are only lethal in the presence of ongoing DNA replication or RNA transcription. See, e.g., D'Arpa, P., et al., Involvement of Nucleic Acid Synthesis in Cell Killing Mechanisms of Topoisomerase I Poisons. *Cancer Res.* 50:6919-6924 (1990). S-phase synchronized cells appeared to be much more sensitive to Topo I inhibitors, compared to G1- or G2/M-cells, suggesting an S-phase specific cytotoxicity for this type of drugs. See, e.g., Takimoto, C. H., et al., Phase I and Pharmacologic Study of Irinotecan Administered as a 96-Hour Infusion Weekly to Adult Cancer Patients. *J. Clin. Oncol.* 18:659-667 (2000). In colon, prostate, ovary and esophagus tumors, elevated Topo I levels have been found, whereas in kidney tumors and non-Hodgkin lymphomas this was not the case See, e.g., Van der Zee, A., et al., P-glycoprotein Expression and DNA Topoisomerase I and II Activity in Benign Tumors of the Ovary and in Malignant Tumors of the Ovary, Before and After Platinum/Cyclophosphamide Chemotherapy. *Cancer Res.* 51:

5915-5920 (1991). Recent investigations have indicated that Irinotecan™ and Topotecan are also inhibitors of angiogenesis, a property that might contribute to their chemotherapeutic activity. Neovascularization has been positively correlated with increasing invasion and metastases of various human tumors. In mice cornea models, anti-angiogenic effects of some CPTs, including Irinotecan™ (CPT-11), were studied. Angiogenesis was induced by fibroblast growth factor, but by increasing the dose of Irinotecan™ CPT-11, the area of angiogenesis in the tumor decreased, following a negative, almost exponential, curve. At dose levels of 210 mg/kg a significant reduction of neovascularization was observed.

Although CPT and the aforementioned CPT analogs have no discernable direct effects on Topo II, these CPT analogs are believed to stabilize the "cleavable complex" in a manner analogous to the way in which epipodophyllotoxin glycosides and various anthracyclines inhibit Topo II.

Inhibition of Topo I by CPT and analogs induces protein-associated-DNA single-strand breaks. Virtually all of the DNA strand breaks observed in vitro cells treated with CPT are protein linked. However, an increase in unexplained protein-free breaks can be detected in L1210 cells treated with CPT. The analogs appear to produce identical DNA cleavage patterns in end-labeled linear DNA. It has not been demonstrated that CPT or CPT analogs cleaves DNA in the absence of the Topo I enzyme.

III. Cell Cycle-Specific Activity of Camptothecin

The activity of CPT is cell cycle-specific. The greatest quantitative biochemical effect observed in cells exposed to CPT is DNA single-strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These aforementioned results are likely due to two factors:

(i) This class of drugs inhibit the normal activity of Topo I, reversibly. Although they may produce potentially lethal modifications of the DNA structure during DNA replication, the DNA strand breaks may be repaired after washout of the drug; and (ii) Cells treated with Topo I inhibitors, such as CPT tend to stay in $G_0$ of the cell cycle until the drug is removed and the cleaved DNA is repaired. Inhibitors of these enzymes can affect many aspects of cell metabolism including replication, transcription, recombination, and chromosomal segregation.

IV. Previously-Tested Camptothecin Analogs

As discussed above, CPT and many of its analogs (see e.g., Wall and Wani, Camptothecin and Taxol: Discovery to Clinic-Thirteenth Bruce F. Cain Memorial Award Lecture Cancer Research 55:753-760 (1995)) are poorly water soluble and are reportedly also poorly soluble in a number of pharmaceutically-acceptable organic solvents as well. However, there are numerous reports of newly created water soluble analogs of CPT (Sawada, S., et al., Synthesis and Antitumor Activity of Novel Water Soluble Analogs of Camptothecin as Specific Inhibitors of Topoisomerase I. *Jour. Med. Chem.* 38:395-401 (1995)) which have been synthesized in an attempt to overcome some of the significant technical problems in drug administration of poorly water soluble camptothecins to subjects with cancer. Several water soluble CPT analogs have been synthesized in an attempt to address the poor water solubility and difficulties in administration to subjects. Several examples of these water soluble CPT analogs are set forth below in Table I:

TABLE I 9-dimethylaminomethyl-10-hydroxycamptothecin (Topotecan)
7-[(4-methylpiperazino)methyl]-10,11-ethylenedioxycamptothecin
7-[(4-methylpiperazino)methyl]-10,11-methylenedioxycamptothecin
7-ethyl-10-[4-(1-piperidino)-1-piperidino]carbonyloxycamptothecin (Irinotecan or CPT-11)
9-nitrocamptothecin (Rubitecan)

Other substituted CPT analogs with different solubility and pharmacologic properties have been synthesized as well; examples of these camptothecin analogs include 9-aminocamptothecin and 9-nitrocamptothecin (Rubitecan) that are poorly soluble in both aqueous and non-aqueous media and have been tested in humans. Rubitecan (9-nitrocamptothecin) is a prodrug of 9-aminocamptothecin, and has been shown to spontaneously convert to 9-aminocamptothecin in aqueous media and in vivo in mice, dogs and humans (see, Hinz, et al., Pharmacokinetics of the in vivo and in vitro Conversion of 9-Nitro-20(S)-camptothecin to 9-Amino-20 (S)-camptothecin in Humans, Dogs and Mice, *Cancer Res.* 54:3096-3100 (1994)).

The pharmacokinetic behavior of 9-nitrocamptothecin and 9-aminocamptothecin is similar to the water-soluble camptothecin analogs (i.e., Topotecan and Irinotecan™) in that the plasma half lives are markedly shorter than the more lipid soluble CPT analogs. An additional major problem with 9-aminocamptothecin is that its chemical synthesis using the semi-synthetic method is performed by nitration of CPT, followed by reduction to the amino group, which is a very low yield type of synthesis. 9-aminocamptothecin is also light sensitive, heat sensitive and oxygen sensitive which render both the initial synthesis and subsequent stability (i.e., shelf-life) of 9-aminocamptothecin problematic, at best. Moreover, the chemical decomposition reactions of 9-aminocamptothecin frequently result in the formation of analogs that exhibit a large degree of toxicity in nude mice, whereas pure 9-aminocamptothecin is significantly less toxic.

As previously discussed, 9-aminocamptothecin is also difficult to administer to subjects because it is poorly soluble in both aqueous and organic solvents. Alternately, while 9-nitrocamptothecin is easier to produce and is more chemically stable, the chemical conversion to 9-aminocamptothecin causes the drug is reportedly susceptible to MDR/MRP tumor-mediated drug resistance, which further limits its utility in the unfortunately common setting of drug resistant neoplasms. Based on pharmacokinetic behavior and chemical properties, 9-aminocamptothecin is predicted to have reduced tissue penetration and retention relative to more lipid soluble camptothecin analogs. Further, its poor solubility diminishes the amount of the drug that can cross the blood/brain barrier.

Of this diverse group of substituted CPT analogs undergoing human clinical development, Irinotecan™ (CPT-11) has been one of the most extensively studied in both Phase I and Phase II clinical trials in human patients with cancer. It is noteworthy that 7-ethyl-10-[4-(1-piperidino)-1-piperidino] carbonyloxy camptothecin (Irinotecan™), which is a water soluble prodrug, is biologically inactive and requires activation by a putative carboxylesterase enzyme. The active species of Irinotecan™ is the depiperidenylated 10-hydroxy-7-ethyl camptothecin (as claimed in Miyasaka, et al., U.S. Pat. No. 4,473,692, (1984)), which is also known as SN38. SN38 is a toxic lipophilic metabolite, which is formed by an in vivo bioactivation of Irinotecan™ by a putative carboxylesterase enzyme.

SN38 is very poorly soluble in water and has not been directly administered to human patients with cancer. Recently, it has been reported in human patients that SN38 undergoes further metabolism to form a glucuronide species, which is an inactive form of the drug with respect to anti-tumor activity, and also appears to be involved in producing human toxicity (e.g., diarrhea, leukopenia) and substantial interpatient variability in drug levels of the free metabolite and its glucuronide conjugate.

Irinotecan™ has been tested in human clinical trials in the United States, Europe and Japan. Clinical studies in Japan alone, have reported approximately 100 patient deaths which have been directly attributable to Irinotecan™ drug toxicity. The Miyasaka, et al. patents (U.S. Pat. No. 4,473,692 and U.S. Pat. No. 4,604,463) state that the object of their invention is to " . . . provide 10-substituted camptothecins which are strong in anti-tumor activity and possess good absorbability in living bodies with very low toxicity" and " . . . to provide new camptothecin analogs which are strong in anti-tumor activity and possess good solubility in water and an extremely low toxicity".

Having multiple drug-related human deaths and serious patient toxicity, is clearly a failure of the aforementioned 10-substituted camptothecins synthesized by Miyasaka, et al., to fulfill their stated objectives. It is notable that tremendous interpatient variability with regard to drug levels of various forms, drug metabolism, certain pharmacokinetic properties and toxicity has been reported with the use of Irinotecan™ in human subjects with cancer. Parenteral administration of Irinotecan™ can achieve micromolar plasma concentrations of Irinotecan™ that, through metabolism to form SN38, can yield nanomolar concentrations of the active metabolite SN38. It has recently been reported in human subjects that SN38 undergoes further metabolism to form the SN38 glucuronide (see, e.g., Gupta, et al., Metabolic Fate of Irinotecan in Humans: Correlation of Glucuronidation with Diarrhea. *Cancer Res.* 54:3723-3725 (1994)).

This further metabolic conversion of Irinotecan™ is important, since there is also reportedly large variability in the conversion of Irinotecan™ to SN38 and large interpatient variability in the metabolism of SN38 to form the inactive (and toxic) SN38 glucuronide conjugate in human subjects. (see, e.g., Gupta, et al., Metabolic Fate of Irinotecan in Humans: Correlation of Glucuronidation with Diarrhea. *Cancer Res.* 54:3723-3725 (1994) and Ohe, et al., Phase I Study and Pharmacokinetics of CPT-11 with 5-Day Continuous Infusion. *JNCI* 84(12):972-974 (1992)).

Since the amount of Irinotecan™ and SN38 metabolized is not predictable in individual patients, significant clinical limitations are posed and create the risk of life-threatening drug toxicity, and/or risk of drug inactivity due to five putative biological mechanisms: (i) conversion of greater amounts of Irinotecan™ to SN38; (ii) inactivation of SN38 by glucuronidation; (iii) conversion of SN38 glucuronide to free SN38; (iv) lack of anti-neoplastic activity due to the conversion of lesser amounts of Irinotecan™ to form SN38; and (v) lack of anti-neoplastic activity by more rapid and extensive conversion of SN38 to form the glucuronide species. It is important to note that even a doubling of the plasma concentration of the potent Irinotecan™ metabolite SN38 may result in significant toxicity, because free SN38 exhibits anti-neoplastic activity at nanomolar concentrations.

Another source of interpatient variability and toxicity is the in vivo de-glucuronidation of SN38 and similar CPT analogs to produce a free and active species of the drug. Deglucuronidation of a CPT analog that is susceptible to A-ring glucuronidation, such as SN38, results in an increase in the plasma or local tissue concentration of the free and active form of the drug, and if high enough levels were reached, patient toxicity, and even death may result.

In addition to the two aforementioned FDA-approved drugs, there are currently at least nine camptothecin analogs that have been evaluated in various stages of clinical testing. These camptothecin analogs include:

1. Karenitecin (BNP1350)

BNP1350 is a highly lipophilic camptothecin analog having a 7-trimethylsilylethyl moiety and is claimed in U.S. Pat. No. 5,910,491, along with formulations and uses thereof. Formulations of BNP1350 with the solvent N-methylpyrrolidinone (NMP) are claimed in, e.g., U.S. Pat. No. 5,726,181.

2. Lurtotecan (NX 211)

NX211 is a water-soluble camptothecin having a 10,11-ethylenedioxy moiety and a cleavable 4-methylpiperazino methyl moiety at C7. By way of example, U.S. Pat. No. 5,559,235 discloses and claims the analogs and formulations, and uses thereof.

3. Exatecan (DX-8951f)

DX-8951f is a hexacyclic camptothecin analog, having 10-methyl and 11-fluoro substitutions, and with its sixth ring fused between C7 and C9. By way of example, and not of limitation, U.S. Pat. No. 5,637,770 describes and claims the analog, and formulations and uses thereof.

4. Diflomotecan (BN 80915)

BN 80915 is a 10,11-difluorocamptothecin, with a 7-member E-ring. By way of example, and not of limitation, U.S. Pat. No. 5,981,542 describes and claims the analog, and its uses and formulations.

5. Rubitecan (9-Nitro CPT)

9-Nitrocamptothecin, as mentioned above is poorly soluble in both aqueous and organic solvents and is described and is not claimed any United States Patents, with the first publication of the analog occurring in Japanese Patent Application No. 82-160944 in 1982. Several patents have issued since then, all regarding processes for preparing the analog as well as uses thereof.

6. Afeletecan (CPT Glycoconjugate)

Afeletecan is an C20 glycoconjugated, water-soluble analog of camptothecin and is described and claimed in U.S. Pat. No. 6,492,335.

7. Gimatecan (ST 1481)

ST1481 is a water-soluble prodrug having a C7 imino moiety, bonded to a terminal tert-butoxy group. The analog is described and claimed in U.S. Pat. No. 6,242,257.

8. Mureletecan (PNU 166148)

Mureletecan is another water-soluble prodrug having a cleavable peptide moiety bonded to C20 to form an ester.

9. Pegbetotecan, Pegcamotecan, Peglinxotecan (PEG CPT; Prothecan®)

This prodrug includes a cleavable water-soluble polyethylene glycol moiety that forms an ester at C20. By way of example, the analog is described and claimed in U.S. Pat. No. 5,840,900.

The various chemical structures of the nine aforementioned camptothecin analogs are set forth in Table II, below:

TABLE II
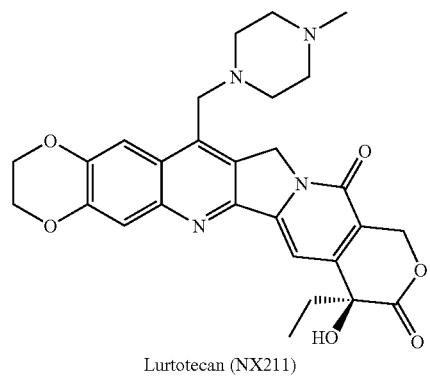
Lurtotecan (NX211)
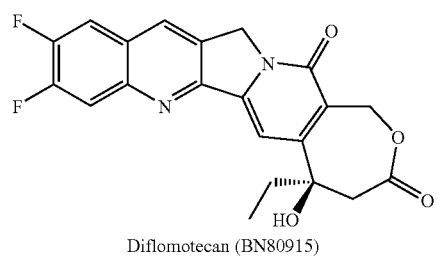
Diflomotecan (BN80915)
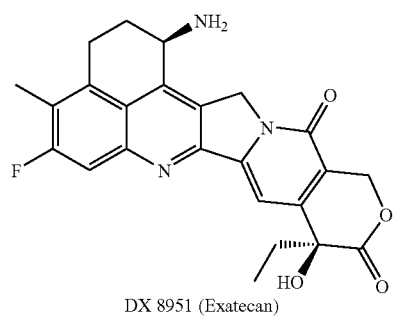
DX 8951 (Exatecan)
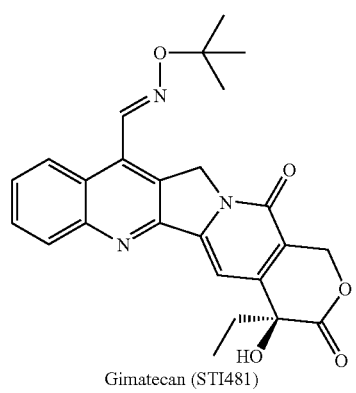
Gimatecan (ST1481)

TABLE II-continued
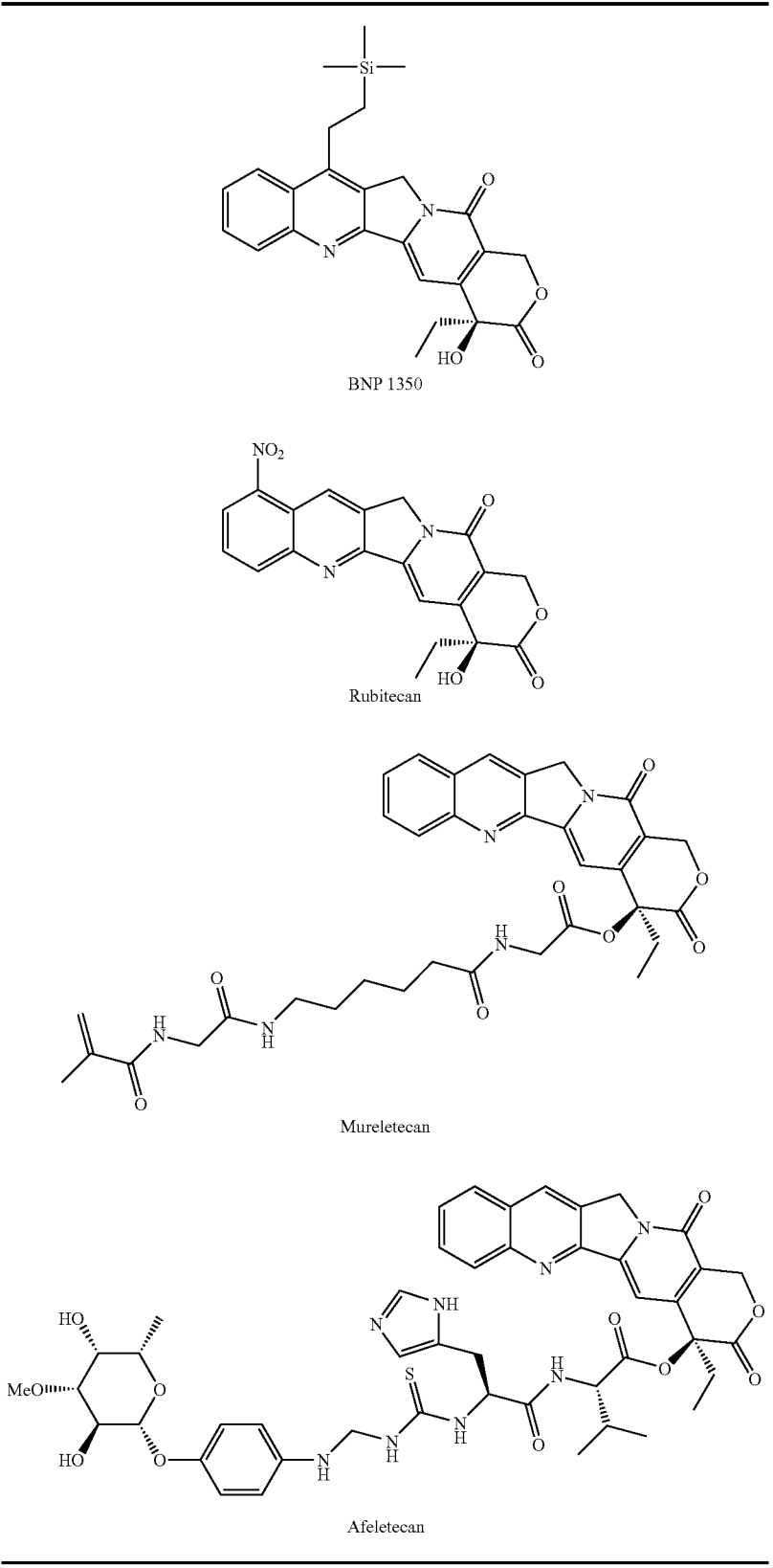

Poorly water-soluble (i.e., hydrophobic) camptothecins are necessarily formulated for administration by dissolution or suspension in organic solvents. U.S. Pat. Nos. 5,447,936; 5,726,181; 5,859,022; 5,859,023; 5,880,133; 5,900,419; 5,935,967; 5,955,467; and other describe pharmaceutical formulations of highly lipophilic, poorly water-soluble camptothecin analogs in various organic solvents, namely N,N-dimethylacetamide (DMA); N,N-dimethylisosorbide (DMI); and N-methylpyrrolidinone (NMP).

V. Formulation and Administration of CPT and Analogs

In the early-1970's, clinical studies utilizing the sodium salt of camptothecin were begun at the Baltimore Cancer Research Center. In this clinical trial, CPT was administered as a rapidly running IV solution over a 5-10 minute period at a concentration of 2 mg of camptothecin sodium per milliliter of saline. Doses of CPT sodium from 0.5 to 10.0 mg/kg of actual or ideal body weight (whichever was less) were used. These investigators reported that because hemorrhagic sterile cystitis was noted in several of the early trials, patients receiving camptothecin sodium were well-hydrated either intravenously (i.v.) or orally for 72 hours after drug administration. It is noteworthy that the mean urine recovery of CPT was 17.4% over the first 48 hours (with the range from: 3.6% to 38.9%) with most of the excretion occurring in the initial 12 hours. When these investigators excluded the five patients with impaired excretion, the mean urine recovery of CPT was 22.8%. These investigators noted that non-metabolized camptothecin in high concentrations rapidly appeared in the urine after iv drug administration and went further to state that this finding probably accounted for the sterile hemorrhagic cystitis noted in three moderately dehydrated patients. Although maintaining a copious urine outflow seems able to prevent this complication, the investigators reported that they were exploring various alterations in urine pH as another possible way of decreasing the risk of this debilitating type of toxicity.

Muggia, et. al. (Phase I Clinical Trial of Weekly and Daily Treatment with Camptothecin (NSC-100880): Correlation with Preclinical Studies. *Cancer Chemotherapy Reports, Part 1.* 56(4):515-521 (1972)) reported results of a Phase I clinical trial in fifteen patients treated with CPT sodium at four weekly dose levels ranging from 20-67 mg/m$^2$. No clinical benefit was observed in eight patients with measurable disease who were treated with the 5-day courses at dose levels associated with toxicity. The CPT was administered in concentrations of 1 or 10 mg/mL and it was always administered by intravenous push. Cystitis was the most prominent non-hematologic toxic effect observed in this study. Bladder toxicity was dose limiting in three patients receiving doses of 20 to 30 mg/m$^2$, and occurred in two additional patients at doses of 30 and 44 mg/m$^2$. Cystitis, another toxic effect occurring frequently after treatment with camptothecin, was not predicted by preclinical toxicological studies. Clinical experience present inventors would suggest that the occurrence of cystitis may be related to the duration of the patient's exposure to the drug. It is their experience that CPT is excreted unchanged by the kidneys, although a large percentage of the drug administered cannot be accounted for in the urine. It is possible that relatively less drug is excreted in the urine of animals since an extremely active transport of CPT into bile has been demonstrated. Alternatively, one needs to postulate that the mucosa of the human bladder is more susceptible to the toxic action of CPT or that the effect on the human bladder is due to some unrecognized CPT metabolite.

In 1972, Moertel and coworkers administered CPT sodium dissolved in physiologic saline at a concentration of 2 mg/mL and administered by rapid intravenous infusion over 5-10 minutes. Two schedules of administration were used in this study: (i) a single injection repeated at 3-week intervals; and (ii) a 5-day course repeated every 4 weeks. The initial dose for the single-dose method was 180 mg/m$^2$. Because of toxic effects, which were considered excessive by the investigators, later patients were treated at doses ranging between 90 and 120 mg/m$^2$. Dosages for the 5-day course ranged between 11 and 22 mg/m$^2$/day (total course: 55-110 mg/m$^2$). The toxicity and response data from this aforementioned study is summarized, below, in Table III-Table VI. Diarrhea was only a problem at higher doses, although it could be quite severe to the point of fecal incontinence and could persist for as long as 4 weeks. Cystitis usually began about 7-10 days after treatment and was characterized clinically by dysuria and frequency. With more severe toxicity, gross hematuria developed. Pathologically, this was characterized by multiple necrotic ulcerations which could involve the entire urinary tract from kidney pelvis to bladder. According to these investigators, the occurrence of hemorrhagic cystitis did not preclude further treatment with CPT, and its severity could be titrated down by lowering the dose in subsequent courses. These investigators also reported that the more prolonged schedule produced more severe toxicity at a given total dose level, but the difference was not as great as might have been predicted by preclinical animal studies.

These investigators proposed that a reasonable initial dose of CPT sodium is 110-120 mg/m$^2$ for the single-injection method or 17 mg/m$^2$/day (total dose: 85 mg/m$^2$) for the 5-day course. They noted that after 2 months (8 or 9 weeks) only two of their 61 patients showed evidence of partial objective improvement and none showed improvement at 3 months. Both patients who demonstrated an objective response at 2 months had large bowel cancer. These investigators concluded that CPT " . . . is a drug of protean and unpredictable toxicity that has no clinical value in the management of gastrointestinal cancer."

TABLE III

Toxic Reactions: Single-Dose Method
Number of Patients with Non-Hematologic Toxicity:

| Dose (mg/m$^2$) | No. of Patients Treated | Diarrhea | Cystitis |
|---|---|---|---|
| 90 | 10 | | |
| 100 | 6 | | 2 |
| 110 | 2 | 1 | 1 |
| 120 | 7 | 4 | 2 |
| 180 | 9 | 2 | 3 |

TABLE IV

Toxic Reactions: 5-day Course
Non-Hematologic Toxicity No. of Patients With:

| Dose (mg/m$^2$ × 5) | No. of Patients Treated | Diarrhea | Cystitis |
|---|---|---|---|
| 11 | 2 | | 1 |
| 15 | 9 | 1 | 4 |
| 17 | 5 | 4 | 2 |
| 20 | 10 | 4 | 6 |
| 22 | 1 | 1 | |

TABLE V

Relationship of Method of Administration to Cystitis

| | Method of Administration | |
|---|---|---|
| Cystitis | Single Dose (% of 34 Patients) | 5-Day Course (% of 27 Patients) |
| | 24 | 48 (P < 0.05) |

TABLE VI

Objective Results

Single-Dose Method (34 Patients Total)

| | Time after start of therapy | | | |
|---|---|---|---|---|
| Objective Results* | 3 wks | 6 wks | 9 wks | 12 wks |
| Improved | 4 | 2 | 2 | — |
| Stable | 17 | 11 | 8 | 6 |
| Worse | 13 | 21 | 24 | 28 |

5-Day Course (27 Patients Total)

| | Time after start of therapy | | |
|---|---|---|---|
| Objective results* | 4 wks | 8 wks | 12 wks |
| Improved | 1 | — | — |
| Stable | 12 | 7 | 6 |
| Worse | 14 | 20 | 21 |

*A total of 3 patients showed a 25%-50% response at 3 wks, only.

In another study, Gottlieb and Luce (Treatment of Malignant Melanoma with Camptothecin (NSC-100880) *Cancer Chemotherapy Reports, Part 1* 56(1):103-105 (1972)) reported the results of treatment of patients with malignant melanoma with CPT sodium (1972). Fifteen patients with advanced malignant melanoma were treated with CPT at doses of 90-360 mg/m$^2$ repeated every 2 weeks. CPT-sodium was administered as a single rapid intravenous (IV) injection starting at a dose of 120 mg/m$^2$ repeated at 2-week intervals. The dose in subsequent courses was increased by increments of 60 mg/m$^2$ per dose (to a maximum of 360 mg/m$^2$) in eight patients who tolerated their initial doses with minimal toxicity. To prevent the known bladder toxicity of this drug, patients were well hydrated for 3 days after therapy. None of the patients had a 50% or greater decrease in tumor diameter. Less pronounced transient tumor regression was noted in three patients, but no clinical benefit was associated with these responses. The remaining patients had no change or progression in their disease. Toxic effects included myelosuppression (11 patients), nausea and vomiting, alopecia, diarrhea, and hemorrhagic cystitis. These investigators concluded that CPT, at least as administered in this study, had little to offer the patient with advanced disseminated melanoma.

Creaven, et al., (Plasma Camptothecin (NSC-100880) Levels During a 5-Day Course of Treatment: Relation to Dose and Toxicity. *Cancer Chemotherapy Reports Part 1* 56(5): 573-578 (1979)) reported studies of plasma CPT levels during a 5-day course of treatment. These investigators state that the toxicity of CPT has been widely and unpredictably variable in the course of initial clinical evaluation. Severe toxic effects occurred even though patients with obvious renal disease were excluded. In this study they investigated plasma CPT levels 24 hours after the administration of sodium CPT administered on a once daily over a 5 day total schedule to determine whether such measurements would be of value in predicting toxicity, and observed that plasma CPT levels have little relation to the dose given when the dose is in the range of 6.5-20 mg/m$^2$/day.

There are several features which establish a commonality with these aforementioned studies with those utilizing sodium CPT. First, is the use of sodium-CPT which made the CPT more water soluble by hydrolysis of lactone E ring to form the carboxylate species (i.e., by formulating CPT in sodium hydroxide). The anti-tumor activity of the carboxylate form of CPT is reduced by at least 10-fold, which partially accounts for the lack of clinical response in these studies. Second, is the rapid intravenous administration of the drug. CPT is an S-phase specific drug and therefore will exert a greater chemotherapeutic effect under conditions of prolonged exposure, as in a continuous intravenous infusion. The short infusion (i.v. "push" or rapid i.v. infusion) times in all of these studies do not allow a long enough exposure time to the drug at suitable levels, and is further compounded by the administration of the water soluble carboxylate form of CPT. A third common feature is the notable frequency of cystitis in these studies using sodium CPT.

VI. Lactone Form Stabilizes CPT Anti-Tumor Activity and Reduces Water Solubility Utilizing HPLC and NMR techniques, researchers have demonstrated that CPT analogs undergo an alkaline, pH-dependent hydrolysis of the E-ring lactone. The slow reaction kinetics allow one to assess whether both the lactone and non-lactone forms of the drug stabilizes the Topo I-cleaved DNA complex. Studies indicate that only the closed lactone form of the drug helps stabilize the cleavable complex. This observation provides reasoning for the high degree of CPT activity observed in solid tumor models. Tumor cells, particularly hypoxic cells prevalent in solid neoplasms, have lower intracellular pH levels than normal cells. At pH levels below 7.0, the closed form of CPT predominates. Thus, the present inventors maintain that CPT will be more effective at inhibiting Topo I in an acidic environment than in cells having higher intracellular pH levels. It is the object of the instant invention to provide lactone stable CPT as the basis of the claimed subject matter. Lactone-stable CPT is defined as CPT which is dissolved in DMI or DMA in the presence of a pharmaceutically-acceptable acid. The presence of the acid stabilizes the lactone form of CPT.

While some authors have stated that the anti-neoplastic effects of CPT is inversely proportional to the molecules hydrophilicity, this cannot state this with certainty because 9-nitrocamptothecin (9-NC) and 9-aminocamptothecin (9-AC) are neither hydrophilic or lipophilic, and no significant antitumor activity has been demonstrated with either one of these compounds. Thus, while water solubility is not required for antitumor activity, a lactone configuration or the equivalent appears to be required for improved antitumor activity of all camptothecins. For example, the lactone form of CPT is poorly soluble in water and yet has significant anti-tumor activity. Thus, providing evidence that the hydrolysis of E-ring lactone to the carboxylate form of CPT greatly increases the water solubility of molecule at the expense of significantly reducing its anti-tumor activity. As previously mentioned, the novel, "flipped" E-ring camptothecin analogs of the present invention belong to a class of drugs with a pH- and protein-dependent interconversion between the pharmacologically-active α-hydroxy-δ-lactone form (i.e., lactone form) and the inactive α-hydroxy-δ-carboxylate form (i.e., carboxyl form), which necessitates analysis of blood samples (i.e., rapid centrifugation to collect the plasma). For example, when total concentrations (i.e., α-hydroxy-δ-lactone+α-hydroxy-δ-carboxylate) are to be measured, this rapid blood processing is crucial, since only the lactone form is able to diffuse across the cell membranes of erythrocytes, and thus a change in the lactone form (i.e., α-hydroxy-δ-lactone) to carboxylate form (i.e., α-hydroxy-δ-carboxylate) ratio has an effect on the total drug concentrations in the plasma compartment. Stabilization of the lactone to carboxylate ratio by direct freezing of the plasma sample is the most convenient approach for the determination of the α-hydroxy-δ-lactone only concentrations. At the time of analysis, all samples can be handled at once by solid-phase or liquid-liquid extraction techniques, in which only the lipophilic lactone form is extracted, while the inactive α-hydroxy-δ-lactone form is discarded. The total drug concentrations are measured in a second analysis after acidification of the samples. A second simple way of stabilizing the lactone to carboxylate ratio is by cold methanolic deproteinization of plasma samples, immediately after collection of the plasma. An advantage of this procedure is the possibility of measuring the α-hydroxy-δ-lactone and α-hydroxy-δ-carboxylate forms simultaneously in one analytical run. Quantification of the CPTs is usually carried out by reversed phase high-performance liquid chromatography (HPLC), and since most CPT analogs have strong fluorescence characteristics, fluorescence detection is the most frequently applied detection technique. See, e.g., Loos, W. J., et al., Determination of Camptothecin Analogs in Biological Matrices by High-Performance Liquid Chromatography. *Anticancer Drugs* 11:315-324 (2000).

A non-enzymatic, pH-dependent, reversible interconversion exists between two forms of the six-membered E-ring camptothecin analogs. The first form, is the pharmacologically-active, novel, "flipped" α-hydroxy-δ-lactone, E-ring form of the present invention (which predominates at acidic pH), wherein the E-ring is in the closed orientation. The second form, is the pharmacologically-inactive α-hydroxy-δ-carboxylate, E-ring form of the present invention (which predominates at basic pH), wherein the E-ring is in the open orientation. The inactive, "open" α-hydroxy-δ-carboxylate form not only lacks the ability to stabilize the cleavable complex, but it is also not able to passively diffuse across cell membranes and is thus pharmacologically-inactive. The equilibrium between the "closed" α-hydroxy-δ-lactone form and the "open" α-hydroxy-δ-carboxylate form is not only dependent upon the pH of the solution, but also upon different affinities of the two different species for proteins. For example, CPT has shown to be inactivated by human serum albumin, by a preferential binding of the carboxylate form to human serum albumin, resulting in a shift of the equilibrium towards the carboxylate form. See, Loos, W. J., et al., A. Role of Erythrocytes and Serum Proteins in the Kinetic Profile of Total 9-Amino-20(S)-Camptothecin in Humans. *Anticancer Drugs* 10:705-7109 (1999).

Various investigators have claimed that reason previous use of sodium hydroxide-treated CPT (sodium-CPT) caused hemorrhagic cystitis relates to the enhanced renal excretion of the carboxylate form of CPT which when exposed to the lower pH (~pH 5) of the distal convoluted tubule in the kidney, the carboxylate form of CPT is converted to the lactone form of CPT. The formation of the lactone form in high concentration at the distal convoluted tubule resulted in a high concentration of the lactone form of CPT being excreted into the collecting duct and into the ureters and bladder which resulted in hemorrhagic cystitis. Elimination of CPT by the renal route is enhanced by administration of the carboxylate form and such elimination may be reduced by administration of the CPT lactone form.

Two CPT analogs (i.e., CPT-11 and Topotecan), have less sporadic toxicities but retain significant activity of the parent analog. CPT-11 and Topotecan are currently approved for human use by the U.S. Food and Drug Administration in the United States. In addition, 10,11-methylenedioxycamptothecin is reportedly very active in preclinical studies, but it is also reported to be relatively insoluble in water which limits its use in the clinic.

Table VII, below, presents data summarizing Phase I clinical trials of CPT-11. Neutropenia and diarrhea were the major reported, dose-limiting toxicities of CPT-11.

TABLE VII

PHASE I STUDIES CPT-11

| Investigator | Schedule | # Pts. | Dose | Toxicity | Tumor Type |
|---|---|---|---|---|---|
| Clavel, et al | 90 min. | 37 | 115 mg/m$^2$/d | neutropenia* | Breast (1 PR) |
| | QDx 3 Q21 Days | | (33-115) | diarrhea, Nausea and vomiting, | Mesothelioma (1 PR) |
| Culine, et al | 90 min. Q21 days | 59 | 150 mg/m$^2$/wk (50-150) | neutropenia* diarrhea* vomiting, Alopecia | Esophagus (1 PR) cervix (1 PR) renal (1 PR) Ovarian |
| | | | | Fatigue Stomatitis neutropenia* | (1 PR) |
| Negoro, et al | 30 min Infusion Weekly | 17 | 100 mg/m$^2$ (50-150) | diarrhea*, N/V, alopecia, Liver Dysfunction | NS CLC (2 PRs) |
| Ohe, et al | 120 hr CI Q3 wks | 36 | 40 mg/m$^2$/d (5-40) | diarrhea* Nausea and vomiting, thrombocytopenia | None |

TABLE VII-continued

PHASE I STUDIES CPT-11

| Investigator | Schedule | # Pts. | Dose | Toxicity | Tumor Type |
|---|---|---|---|---|---|
| Rothenberg, et al | 90 mg QWx 4 Q42 days | 32 | 180 mg/m²/wk (50-180) | Anemia, liver Dysfunction neutropenia, Nausea, vomiting, Alopecia | Colon Ca (2 PRs) |
| Rowinsky, et al | 90 min | 32 | 240 mg/m² | neutropenia* | Colon Cancer (1 PR) |
| | Infusion Q21 day | | (100-345) | vomiting, diarrhea abd. pain, flushing | Cervix Ca (1 PR) |

*Dose Limiting Toxicity

It should be noted that the analogs disclosed in the present invention, which can be administered either orally or parenterally to patients substantially in the lactone form, which greatly ameliorate renal elimination of CPT and the concomitant incidence of hemorrhagic cystitis. In addition to the aforementioned toxicities and limited clinical responses to previously-described CPTs, CPT has also been considered unsuitable for direct clinical use because it is poorly soluble in water. One useful purpose of the present invention is to formulate CPT in a pharmaceutically-acceptable manner to stabilize CPT in the lactone ring form. It is this lactone stable CPT formulation which permits direct administration of CPT to cancer patients. An additional purpose of this invention to provide certain indications, schedules, dosages and routes of administration of a lactone-stable camptothecin for the purpose of treating cancer in humans. Another advantage of present invention provides clinicians with the ability to directly adjust the plasma levels of CPT to the point of therapeutic tolerance by controlling the dose and the schedule of administration. The present inventors contend that this should lead to a superior ability to achieve better chemotherapeutic activity and reduce interpatient variability of the plasma levels of CPT.

As previously discussed, a lactone-stable form of CPT has not been administered by parenteral or oral routes in human subjects for the purpose of inhibiting the growth of cancer cells. The present invention overcomes these limitations and discloses and claims: (i) a novel, lactone-stable, "flipped" E-ring camptothecin, pharmaceutically-acceptable salts, and/or analogs thereof; (ii) methods of synthesis of said novel, lactone-stable, "flipped" E-ring camptothecin, pharmaceutically-acceptable salts, and/or analogs thereof; (iii) pharmaceutically-acceptable formulations comprising said novel, lactone-stable, "flipped" E-ring camptothecin, pharmaceutically-acceptable salts, and/or analogs thereof, and, optionally, one or more additional chemotherapeutic agents; (iv) methods of administration of said novel, lactone-stable, "flipped" E-ring camptothecin, pharmaceutically-acceptable salts, and/or analogs thereof, and, optionally, one or more additional chemotherapeutic agents, to subjects in need thereof; and (v) devices for the administration of said novel, lactone-stable, "flipped" E-ring camptothecin, pharmaceutically-acceptable salts, and/or analogs thereof, and, optionally, one or more chemotherapeutic agents, to subjects in need thereof.

SUMMARY OF THE INVENTION

The present invention described and claimed herein have many attributes and embodiments including, but not limited to, those set forth or described or referenced in this Summary. It is not intended to be all-inclusive and the inventions described and claimed herein are not limited to or by the features or embodiments identified in this Summary, which is included for purposes of illustration only and not restriction.

The present invention discloses compositions, methods, formulations, devices, and uses of the foregoing. The compositions, methods, formulations, and devices of the present invention may be utilized for the medical treatment of a subject suffering from one or more types of cancer including, but not limited to: ovary, breast, lung, esophagus, bladder, stomach, pancreas, liver, testicular, head, neck, oral mucosa, colorectal, anus, kidney, bladder, uroepithelium, lymphoma, central nervous system, prostate, endometrium, uterine, fallopian tube, mesothelioma, peripheral nervous system, melanoma, myeloma, leukemia, and Kaposi's sarcoma.

One embodiment of the present invention discloses a novel lactone-stable, "flipped" E-ring camptothecin analog consisting of the structure illustrated below:

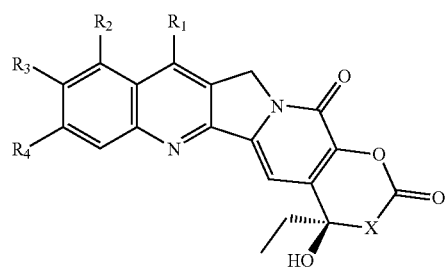

wherein;
X is —$(CH_2)_n$—; wherein n≦2 or $CF_2$;
$R_1$ is —$(CH_2)_n$—, —$(CH_2)_n Si(R_5)_3$, —$(CH_2)_n Ge(R_5)_3$; wherein n=0 to 6; any halide; any short chain amine; and wherein $R_5$ is $CH_3$, $C_2H_5$, $C_3H_8$;
$R_2$ is —$(CH_2)_n$—, —$(CH_2)_n Si(R_5)_3$, —$(CH_2)_n Ge(R_5)_3$; wherein n=0 to 6; any halide; any short chain amine; and wherein $R_5$ is $CH_3$, $C_2H_5$, $C_3H_8$;

$R_3$ and $R_4$ are any halide; any short chain amine; $CH_3O$; —$OCH_2CH_2O$—, —$OCH_2O$—; wherein the aforementioned substituent groups of $R_3$ and $R_4$ may covalently bond together so as to form a "ring-like" structure between said substituent groups; or R1 and R2, or R2 and R3, or any combination of R1, R2; R2 and R3; and R3 and R4 substituents may covalently bind to form additional ring like structure(s); or a pharmaceutically-acceptable salt, analog, prodrugs, conjugates, hydrates, solvates, polymorphs, and/or tautomeric forms thereof.

Another embodiment discloses a novel, lactone-stable, "flipped" E-ring camptothecin, pharmaceutically-acceptable salt, and/or analog thereof, wherein $R_1$ comprises: a —X-(lower alkyl)-Si(alkyl)$_3$ or —X-(lower alkyl)-Ge(alkyl)$_3$ and one or more of the A-ring moieties is a substituent group other than hydrogen.

One embodiment of the invention discloses a novel lactone-stable, "flipped" E-ring camptothecin analog, or pharmaceutically-acceptable salt thereof, wherein $R_1$ comprises: a -(lower alkyl)-Si moiety or a -(lower alkyl)-Ge moiety; and wherein one or two of $R_2$ through $R_4$ is a moiety selected from the group comprising: amino, substituted amino, hydroxy, alkoxy, -carbonyl-lower alkyl-heterocycle, -lower alkyl-trimethylsilyl, -lower alkyl-trimethylgermanium or aryloxy.

One embodiment discloses a formulation comprising a novel, lactone-stable, "flipped" E-ring camptothecin analog, pharmaceutically-acceptable salt, and/or analog thereof, wherein said analog is dissolved, in the presence of a pharmaceutically-acceptable acid, in one or more solvents including, but not limited to, N-methylpyrrolidinone, dimethylisosorbide, or dimethylacetamide. In a preferred embodiment, the pharmaceutically-acceptable acid is an organic carboxylic acid. In a most preferred embodiment, the pharmaceutically-acceptable acid is citric acid or phosphoric acid.

Another embodiment of the invention discloses the administration of a formulation which contains a sufficient concentration of said novel, lactone-stable, "flipped" E-ring camptothecin, pharmaceutically-acceptable salt, and/or analog thereof to provide a total dosage administration of about 0.1 mg/m$^2$ to about 100 mg/m$^2$. In a preferred embodiment, the camptothecin is dissolved, in the presence of a pharmaceutically-acceptable acid, in one or more solvents including, but not limited to, N-methylpyrrolidinone, dimethylisosorbide, or dimethylacetamide.

One embodiment discloses a formulation comprising a sufficient concentration of said novel, lactone-stable, "flipped" E-ring camptothecin analog to provide a total dosage administration of about 0.1 mg/m$^2$ to about 100 mg/m$^2$, and containing and from approximately 0.01 to approximately 0.9 part by weight of a pharmaceutically-acceptable organic carboxylic acid per part by weight of said lactone-stable, E-ring camptothecin analog, pharmaceutically-acceptable salt, and/or analog thereof. In the most preferred embodiment the pharmaceutically-acceptable organic carboxylic acid is citric acid, or phosphoric acid.

One embodiment of the present invention discloses a formulation comprising a pharmaceutically-acceptable organic carboxylic acid which is from approximately 0.05 to approximately 0.1 part by weight of said novel, lactone-stable, "flipped" E-ring camptothecin analog, pharmaceutically-acceptable salt, and/or analog thereof.

One embodiment discloses a formulation further comprising taurocholic acid, or a pharmaceutically-acceptable salt thereof, and polyethylene glycol.

Another embodiment discloses a formulation comprising for each part by weight of said novel, lactone-stable, "flipped" E-ring camptothecin, pharmaceutically-acceptable salt, and/or analog thereof, approximately 1 to approximately 10 parts by weight of N-methylpyrrolidinone, dimethylisosorbide, or dimethylacetamide, approximately 0.005 to approximately 0.5 parts by weight of citric acid, approximately 1 to approximately 10 parts by weight of taurocholic acid, or a pharmaceutically-acceptable salt thereof, and approximately 1 to approximately 10 parts by weight of polyethylene glycol.

Another embodiment discloses a formulation comprising for each part by weight of said novel, lactone-stable, "flipped" E-ring camptothecin, pharmaceutically-acceptable salt, and/or analog thereof, approximately 1 to approximately 10 parts by weight of N-methylpyrrolidinone, dimethylisosorbide, or dimethylacetamide, approximately 0.005 to approximately 0.5 parts by weight of a pharmaceutically-acceptable organic carboxylic acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer. In a preferred embodiment, the pharmaceutically-acceptable organic carboxylic acid is citric acid, the polyethylene glycol has a molecular weight of approximately 300.

Another embodiment discloses a formulation comprising a sufficient concentration of said novel, lactone-stable, "flipped" E-ring camptothecin analog, pharmaceutically-acceptable salt, and/or analog thereof to provide a total dosage administration of about 0.1 mg/m$^2$ to about 100 mg/m$^2$, dissolved in approximately 1 to approximately 10 parts by weight of N-methylpyrrolidinone, dimethylisosorbide, or dimethylacetamide, in the presence of approximately 0.1 to approximately 0.5 parts by weight of a pharmaceutically-acceptable organic carboxylic acid, wherein said composition further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. In a preferred embodiment, the pharmaceutically-acceptable organic acid is citric acid, the polyethylene glycol has a molecular weight of approximately 300, the lower alcohol is ethanol, and wherein said surfactant is polysorbate-80 or poloxamer PF-127.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 100 mg/m$^2$ of said composition over a duration of approximately 120 minutes given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 75 mg/m$^2$ of said composition over a duration of approximately 120 minutes given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 50 mg/m$^2$ of said composition over a duration of approximately 120 minutes given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m$^2$ to approximately 100 mg/m$^2$ of said composition over a duration of approximately 120 minutes every 21 to 28 days.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m$^2$ to approximately 75 mg/m$^2$ of said composition over a duration of approximately 120 minutes every 21 to 28 days.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m$^2$ to approximately 50 mg/m$^2$ of said composition over a duration of approximately 120 minutes for three consecutive days every 21 to 28 days.

Another embodiment discloses a method for the parenteral administration of a formulation comprising said novel, lactone-stable, "flipped" camptothecin, pharmaceutically-acceptable salt, and/or analog thereof, in combination with one or more chemotherapeutic agents, wherein said chemotherapeutic agents include, but are not limited to, a fluropyrimidine; a pyrimidine nucleoside; a purine nucleoside; an antifolate, a platinum analog; an anthracycline/anthracenedione; an epipodopodophyllotoxin; a camptothecin; a hormone, a hormonal analog; an antihormonal; an enzyme, protein, peptide, or antibody; a vinca alkaloid; a taxane; an epothilone; an antimicrotubule agent; an alkylating agent; an antimetabolite; a topoisomerase inhibitor; an antiviral; or another cytotoxic and cytostatic agent.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$ to approximately 100 mg/m$^2$ of said composition in single or divided dosages within a 24 hour period every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$ to approximately 75 mg/m$^2$ of said composition daily in single or divided doses for three consecutive days every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$ to approximately 50 mg/m$^2$ of said composition daily in single or divided doses for three consecutive days every 21 to 28 days.

Another embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$ to approximately 100 mg/m$^2$ of said composition in single or divided dosages within a 24 hour period given once per week for three consecutive weeks with 2 weeks rest after each 3 week cycle.

One embodiment discloses a method for the oral administration of a formulation comprising said novel, lactone-stable, "flipped" camptothecin, pharmaceutically-acceptable salt, and/or analog thereof, to a previously untreated patient with cancer, said method consisting of administering from approximately 0.1 mg/m$^2$ to approximately 75 mg/m$^2$ of said composition in single or divided doses within a 24 hour period once per week for three consecutive weeks with 2 weeks rest after each 3 week cycle.

Another embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$ to approximately 50 mg/m$^2$ of said composition in single or divided dosages within a 24 hour period given once per week for three consecutive weeks with 2 weeks rest after each 3 week cycle.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$/day to approximately 100 mg/m$^2$/day of said composition in single or divided daily doses administered within each 24 hour period for two to five consecutive days and repeated every 21 to 48 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$/day to approximately 75 mg/m$^2$/day of said composition in single or divided daily doses administered within each 24 hour period for two to five consecutive days and repeated every 21 to 48 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m$^2$/day to approximately 50 mg/m$^2$/day of said composition in single or divided daily doses administered within each 24 hour period for two to five consecutive days and repeated every 21 to 48 days.

One embodiment discloses a method for the administration of a formulation comprising said novel, lactone-stable, "flipped" camptothecin, pharmaceutically-acceptable salt, and/or analog thereof, to a human subject with one or more cancers who is also concomitantly suffering from hemorrhagic cyctitis and renal toxicity.

Such novel, lactone-stable, "flipped" E-ring camptothecins can be derivatized at the same positions on the A and B rings, as shown above. Such derivatization can be utilized to impart a number of pharmacological activities to the molecule including, but not limited to: (i) increased lipophilicity, (ii) increased stability, (iii) increased reactivity with DNA, and the like. Various side-chains on the A and B rings are disclosed in U.S. Pat. Nos. 6,194,579; 5,935,967; 5,674,874; 5,633,260; and 5,900,419 (all of which are incorporated herein by reference in their entirety) and would be suitable for substituents on these novel, lactone-stable, "flipped" E-ring camptothecins.

In addition, to disclosing methods for the synthesis of novel, lactone-stable, "flipped" E-ring camptothecins and their various analogs, the present invention also discloses pharmaceutically-acceptable formulations which may be utilized with said novel, lactone-stable "flipped" E-ring camptothecins and their various analogs. These formulations are efficacious for use with highly lipophilic analogs such as the novel, lactone-stable, "flipped" E-ring camptothecins and their various analogs, which are even more lipophilic than their 7-member E-ring counterparts. The formulation is adapted for administration by parenteral (e.g., intravenous) and/or oral routes to human patients as treatment for various cancers/tumors. The formulation has as its active ingredient an effective amount of a highly lipophilic camptothecin analog, typically used in the treatment of cancers/tumors.

Specifically, the present invention involves the formulation and methods of use of the novel, lactone-stable, "flipped" E-ring camptothecin to treat cancer in humans. In the case of intravenous administration of novel, lactone-stable, "flipped" E-ring camptothecin, several schedules and various dosages produce sufficient levels of said novel camptothecin to yield beneficial chemotherapeutic effects in humans. The effective levels of novel, lactone-stable, "flipped" E-ring camptothecin are safe in terms of the incidence and severity of specific side effects that may occur with administration and are acceptable within standard medical practice for patients undergoing treatment for cancer.

Preferred formulations are disclosed in the Specification below, and do not limit the scope of the invention, which is defined by the claims.

DETAILED DESCRIPTION OF THE INVENTION

The preferred embodiments herein described are not intended to be exhaustive, or to limit the invention to the precise forms disclosed. They are chosen to best illustrate the principles of the invention, and its application and practical use to best enable others skilled in the art to follow its teachings.

Definitions

All definitions provided by: *Hawley's Condensed Chemical Dictionary*, 14th Edition, John Wiley & Sons, Inc., Publishers ((2001) and *American Hospital Formulary Service, Drug Information*, American Society of Health-System Pharmacists, Publishers (1999).

"Scaffold" means the fixed structural part of the molecule of the formula given.

"Fragments", "Moieties" or "Substituent Groups" are the variable parts of the molecule, designated in the formula by variable symbols, such as $R_x$, X or other symbols. Fragments may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond (alkenyl) or triple bond (alkynyl) between two of the carbon atoms;

"$C_x$-$C_y$ alkoxy" means a straight or branched hydrocarbon chain with as few as x and as many as y carbon atoms, with the chain bonded to the scaffold through an oxygen atom;

"Alkoxycarbonyl" (aryloxycarbonyl) means an alkoxy (aryloxy) moiety bonded to the scaffold through a carbonyl;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic analogs of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contain from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Azide" means any group of analogs having the characteristic formula R($N_3$)x. R may be almost any metal atom, a hydrogen atom, a halogen atom, the ammonium radical, a complex [Co($NH_3$)$_6$], [Hg(CN)$_2$M] (with M=Cu, Zn, Co, Ni), an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing analogs possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Substituted" modifies the identified fragments (moieties) by replacing any, some or all of the hydrogen atoms with a moiety (moieties) as identified in the specification. Substitutions for hydrogen atoms to form substituted analogs include halo, alkyl, nitro, amino (also N-substituted, and N,N disubstituted amino), sulfonyl, hydroxy, alkoxy, phenyl, phenoxy, benzyl, benzoxy, benzoyl, and trifluoromethyl.

The term "Highly Lipophilic Camptothecin Analogs (HL-CDs)", are defined as camptothecin analogs having a water solubility of less than 5 μg/mL of water.

The term "novel, lactone-stable, "flipped" E-ring camptothecin" (IUPAC Nomenclature: 4R-Ethyl-4-hydroxy-3H-pyrano[2',3':6:7]indolizino[1,2-b]quinoline-2,14(4H,12H)-dione) is defined as having a similar molecular structure to that of camptothecin; IUPAC Nomenclature: (S)-4-Ethyl-4-hydroxy-1H-pyrano[3',4':6,7]indolizino[1,2-b]quinoline-3,14(4H,12H)-dione), with the exception that in the novel, lactone-stable, "flipped" camptothecin of the present invention the methylene group in the E-ring lactone has been transpositioned or migrated from a benzylic position to one between a tertiary hydroxy and carbonyl group leading to the conversion of an α-hydroxy-δ-lactone to a β-hydroxy-δ-lactone. The term, as utilized herein, refers to the novel, lactone-stable, "flipped" E-ring camptothecin molecule itself, pharmaceutically-acceptable salts thereof (including those salts referenced herein), and/or various analogs of a lactone-stable, E-ring camptothecin.

The term "pharmaceutically-acceptable acid" is included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The amount of acid used may be from about 0.005 to about 0.5 parts by weight of acid per part by weight of a novel, lactone-stable, "flipped", E-ring camptothecin and preferably from about 0.01 to 0.3 part by weight of acid per part by weight of a novel, lactone-stable, "flipped", E-ring camptothecin. Citric acid is preferably used in a proportion of from about 0.05 to about 0.1, and about 0.1 part by weight in the presence of taurocholic acid or a pharmaceutically acceptable salt thereof.

As utilized herein the term "cancer" refers to all known forms of cancer including, solid forms of cancer (e.g., tumors), lymphomas, and leukemias.

As used herein "anti-neoplastic agent" or "anti-cancer" or "chemotherapeutic agent" or "chemotherapy agent" refer to an agent that reduces, prevents, mitigates, limits, and/or delays the deleterious physiological manifestations, the growth or metastases of neoplasms, or by killing neoplastic cells directly by necrosis or apoptosis of neoplasms or any other mechanism. Chemotherapeutic agents include, for example, fluropyrimidine; pyrimidine nucleosides; purine nucleosides; anti-folates, platinum analogs; anthracycline/anthracenedione; epipodopodophyllotoxin; camptothecin; hormones; hormonal analogs; antihormonals; enzymes, proteins, and antibodies; vinca alkaloids; taxanes; antimirotubule agents; alkylating agents; antimetabolites; topoisomerase inhibitors; antivirals; and miscellaneous cytostatic agents. "Chemotherapy" refers to treatments using recognized chemotherapeutic agents or chemotherapy agents.

As used herein, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; and/or an increase in duration of chemotherapeutic therapy.

As used herein "adverse symptom" means a manifestation or condition that is reported by the patient (e.g., pain, nausea, chills, depression, numbness, tingling, anorexia, dysguesia, and the like); whereas an "adverse sign" means an objective finding that is a physically observable manifestation of a condition, adverse event or disease in the patient (e.g., palpable purpura, maculopapular rash, spider angioma, Chvostek's sign, Babinski's sign, Trousseau's sign, opisthotonos, and the like).

The administration of the novel, lactone-stable, "flipped" E-ring camptothecin of the present invention is likely to offer several important clinical advantages over administration of, e.g., CPT-11 and the other non-lactone-stable camptothecins. For example:

(1) direct administration of the novel, lactone-stable, "flipped" E-ring camptothecin allows the clinician to tailor the administration of the active cytotoxic species (i.e., the novel, lactone-stable, "flipped" E-ring camptothecin) in accordance with the patient's condition;

(2) direct administration of the novel, lactone-stable, "flipped" E-ring camptothecin overcomes interpatient variability which may be due to polymorphism of key enzyme(s) in the metabolism of, e.g., CPT-11 to HECPT; and (3) clinicians can more consistently optimize the drug dosage and schedule to achieve the maximum tolerated dose of the novel, lactone-stable, "flipped" E-ring camptothecin which is likely to lead to the most beneficial clinical anti-cancer effect.

Regarding the clinical utility of the novel, lactone-stable, "flipped" E-ring camptothecin for the treatment of human cancer, this invention provides the following:

(1) methods of administering of the novel, lactone-stable, "flipped" E-ring camptothecin to patients with cancer;

(2) solutions of the novel, lactone-stable, "flipped" E-ring camptothecin;

(3) formulations comprising of the novel, lactone-stable, "flipped" E-ring camptothecin;

(4) stable formulations of the novel, lactone-stable, "flipped" E-ring camptothecin suitable for parenteral administration;

(5) pharmacologic schedules for achieving the maximum tolerated dose with acceptable clinical toxicity observed in standard clinical practice of cancer treatment;

(6) a novel oral formulation of the novel, lactone-stable, "flipped" E-ring camptothecin; and (7) use of the novel, lactone-stable, "flipped" E-ring camptothecin for the treatment of localized cancer by direct administration into various body cavities.

The various compounds disclosed in the present invention are semisynthetic analogs of camptothecin. In particular, the camptothecin analogs of the present invention possess a novel, lactone-stable, "flipped" E-ring, which may also include di- and tri-substituted analogs derived from said novel camptothecins. The generic structural formula of the novel, lactone-stable, "flipped" E-ring camptothecin (IUPAC Nomenclature: 4R-Ethyl-4-hydroxy-3H-pyrano[2',3':6:7]indolizino[1,2-b]quinoline-2,14(4H,12H)-dione), disclosed in the present invention is illustrated in Formula A, below:

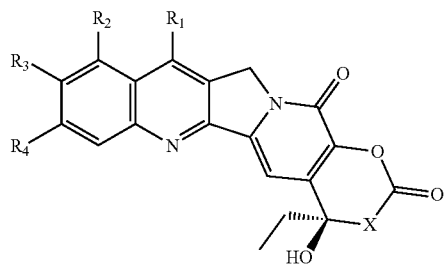

Formula A wherein;

X is —(CH$_2$)$_n$—; wherein n≦2 or CF$_2$;

R$_1$ is —(CH$_2$)$_n$—, —(CH$_2$)$_n$Si(R$_5$)$_3$, —(CH$_2$)$_n$Ge(R$_5$)$_3$; wherein n=0 to 6; any halide; any short chain amine; and wherein R$_5$ is CH$_3$, C$_2$H$_5$, C$_3$H$_8$;

R$_2$ is —(CH$_2$)$_n$—, —(CH$_2$)$_n$Si(R$_5$)$_3$, —(CH$_2$)$_n$Ge(R$_5$)$_3$; wherein n=0 to 6; any halide; any short chain amine; and wherein R$_5$ is CH$_3$, C$_2$H$_5$, C$_3$H$_8$;

R$_3$ and R$_4$ are any halide; any short chain amine; CH$_3$O; —OCH$_2$CH$_2$O—, —OCH$_2$—; wherein the aforementioned substituent groups of R$_3$ and R$_4$ may covalently bond together so as to form a "ring-like" structure between said substituent groups; or R1 and R2, or R2 and R3, or any combination of R1, R2; R2 and R3; and R3 and R4 substituents may covalently bind to form additional ring like structure(s); or a pharmaceutically-acceptable salt, analog, prodrugs, conjugates, hydrates, solvates, polymorphs, and/or tautomeric forms thereof.

By way of example, and not of limitation, various examples of these aforementioned analogs of the novel, lactone-stable, "flipped" E-ring camptothecin of the present invention, with their associated IUPAC names, are illustrated below:

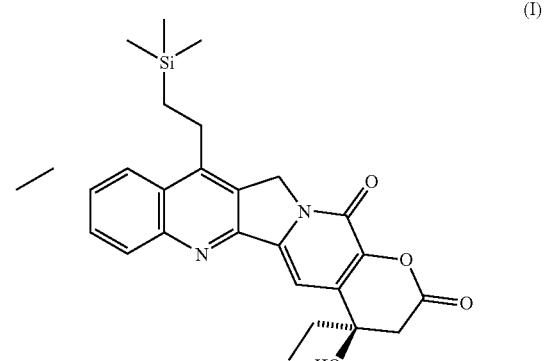

4R-Ethyl-4-hydroxy-11-(2-(trimethylsilyl)ethyl)-3H-pyrano[2',3':6,7]indolizino[1,2-b]quinoline-2,14-(4H,12H)-dione

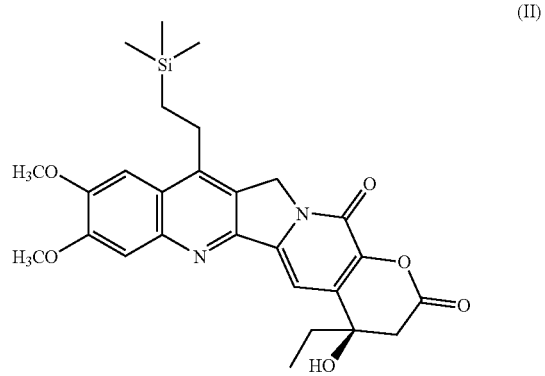

4R-Ethyl-4-hydroxy-8,9-dimethoxy-11-(2-(trimethylsilyl)ethyl)-3H-pyrano[2',3':6,7]indolizino[1,2-b]quinoline-2,14-(4H,12H)-dione

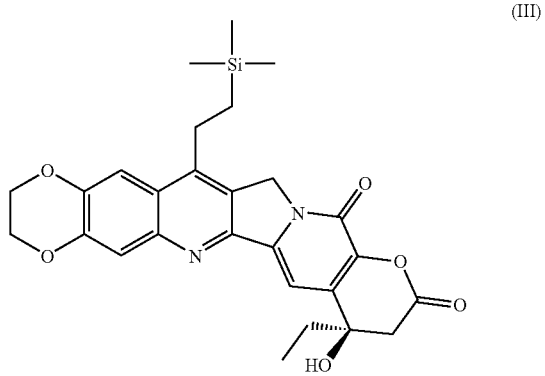

31

4R-Ethyl-4-hydroxy-8,9-ethylenedioxy-11-(2-(trimethylsilyl)ethyl)-3H-pyrano[2',3':6,7]indolizino[1,2-b]quinoline-2,14-(4H,12H)-dione

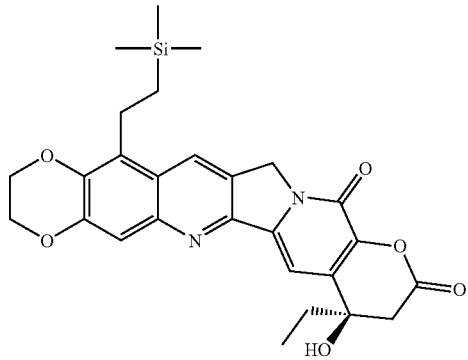

4R-Ethyl-4-hydroxy-8,9-ethylenedioxy-10-(2-(trimethylsilyl)ethyl)-3H-pyrano[2',3':6,7]indolizino[1,2-b]quinoline-2,14-(4H,12H)-dione (V)

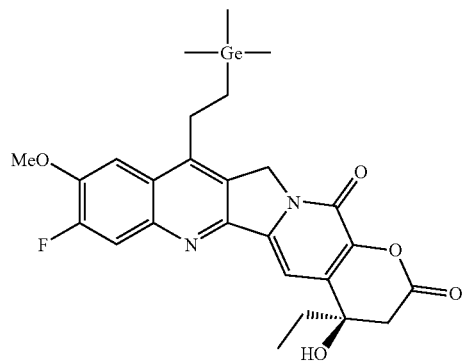

4R-Ethyl-4-hydroxy-8-fluoro-9-methoxy-11-(2-(trimethylgermanyl)ethyl)-3H-pyrano[2',3':6,7]indolizino[1,2-b]quinoline-2,14-(4H,12H)-dione (VI)

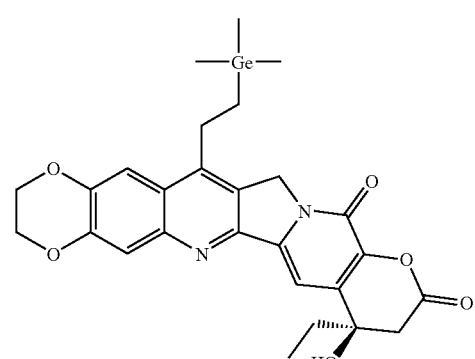

32

4R-Ethyl-4-hydroxy-8,9-ethylenedioxy-1-(2-(trimethylgermanyl)ethyl)-3H-pyrano[2',3':6,7]indolizino[1,2-b]quinoline-2,14-(4H,12H)-dione (VII)

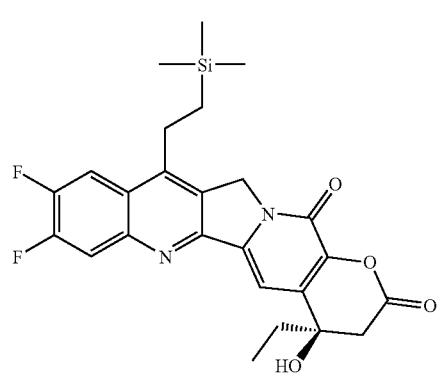

4R-Ethyl-4-hydroxy-8,9-difluoro-11-(2-(trimethylsilyl)ethyl)-3H-pyrano[2',3':6,7]indolizino[1,2-b]quinoline-2,14-(4H,12H)-dione (VIII)

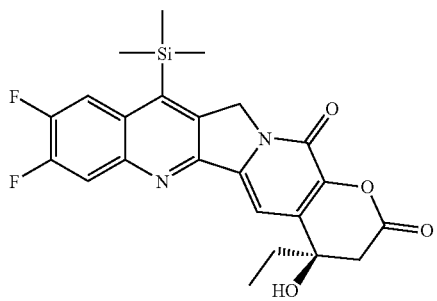

4R-Ethyl-4-hydroxy-8,9-difluoro-11-trimethylsilyl-3H-pyrano[2',3':6,7]indolizino[1,2-b]quinoline-2,14-(4H,12H)-dione (IX)

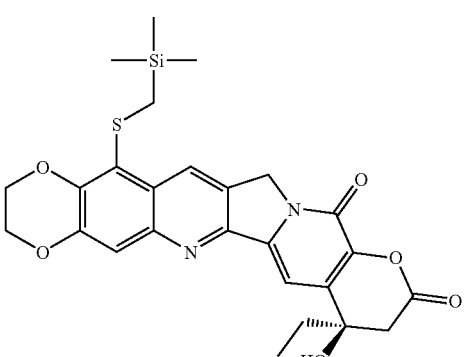

33

4R-Ethyl-4-hydroxy-8,9-ethylenedioxy-10-((trimethylsilyl)methylthio)-3H-pyrano[2',3':6,7]indolizino[1,2-b]quinoline-2,14-(4H,12H)-dione

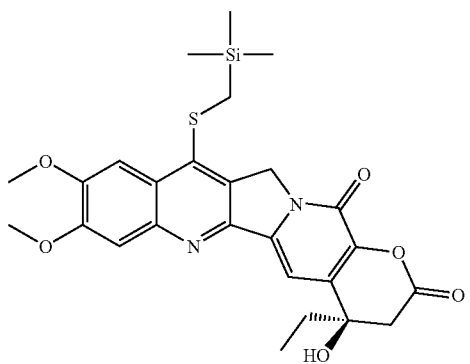

(X)

4R-Ethyl-4-hydroxy-8,9-dimethoxy-11-((trimethylsilyl)methylthio)-3H-pyrano[2',3':6,7]indolizino[1,2-b]quinoline-2,14-(4H,12H)-dione

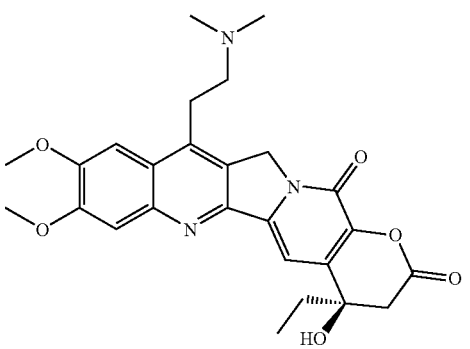

(XI)

4R-Ethyl-4-hydroxy-8,9-dimethoxy-11-(2-(dimethylamino)ethyl)-3H-pyrano[2',3':6,7]indolizino[1,2-b]quinoline-2,14-(4H,12H)-dione

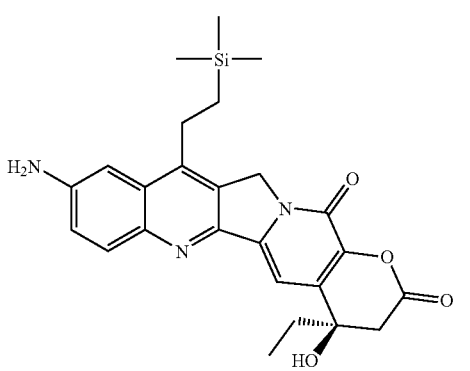

(XII)

34

4R-Ethyl-4-hydroxy-9-amino-11-(2-(trimethylsilyl)ethyl)-3H-pyrano[2',3':6,7]indolizino[1,2-b]quinoline-2,14-(4H,12H)-dione The preferred analogs of the novel, lactone-stable, "flipped" E-ring camptothecin of the present invention include, but are not limited to, those analogs wherein $R_1$ is —X-(lower alkyl)-Si(alkyl)$_3$ or —X-(lower alkyl)-Ge (alkyl)$_3$ and one or more of the A-ring moieties is other than hydrogen. Preferred $R_3$ moieties include hydrogen and lower alkylene, with preferred $R_1$ moieties including any silane moiety when $R_3$ is lower alkylene. This formula produces various di- and tri-substituted analogs of naturally occurring camptothecin. The presence of one or more silicon or germanium moieties on the scaffold enhances the high lipophilicity of the analog, and stabilizes the lactone E-ring. The preferred lactone-stable, E-ring camptothecin of the present invention include, but are not limited to: Structure (II)—4-Ethyl-4-hydroxy-8,9-dimethoxy-11-(2-(trimethylsilyl)ethyl)-3H-pyrano[2',3':6,7]indolizino[1,2-b]quinoline-2,14-(4H,12H)-dione; and Structure (VIII)—4-Ethyl-4-hydroxy-8,9-difluoro-11-trimethylsilyl-3H-pyrano[2',3':6,7]indolizino[1,2-b]quinoline-2,14-(4H,12H)-dione.

More preferred analogs of the novel, lactone-stable, "flipped" E-ring camptothecin of the present invention include, but are not limited to: Structure (III)—4R-Ethyl-4-hydroxy-8,9-ethylenedioxy-11-(2-(trimethylsilyl)ethyl)-3H-pyrano[2',3':6,7]indolizino[1,2-b]quinoline-2,14-(4H,12H)-dione; Structure (IV)—4R-Ethyl-4-hydroxy-8,9-ethylenedioxy-10-(2-(trimethylsilyl)ethyl)-3H-pyrano[2',3':6,7]indolizino[1,2-b]quinoline-2,14-(4H,12H)-dione; Structure (V)—4R-Ethyl-4-hydroxy-8-fluoro-9-methoxy-11-(2-(trimethylgermanyl)ethyl)-3H-pyrano[2',3':6,7]indolizino[1,2-b]quinoline-2,14-(4H,12H)-dione; Structure (VII)—4R-Ethyl-4-hydroxy-8,9-difluoro-11-(2-(trimethylsilyl)ethyl)-3H-pyrano[2',3':6,7]indolizino[1,2-b]quinoline-2,14-(4H,12H)-dione; Structure (IX)—4R-Ethyl-4-hydroxy-8,9-ethylenedioxy-10-((trimethylsilyl)methylthio)-3H-pyrano[2',3':6,7]indolizino[1,2-b]quinoline-2,14-(4H,12H)-dione; and Structure (XI)—4R-Ethyl-4-hydroxy-8,9-dimethoxy-11-(2-(dimethylamino)ethyl)-3H-pyrano[2',3':6,7]indolizino[1,2-b]quinoline-2,14-(4H,12H)-dione.

Most preferred analogs include those analogs where $R_1$ is a -(lower alkyl)-Si moiety or a -(lower alkyl)-Ge moiety, one or two of $R_2$ through $R_4$ is amino, substituted amino, hydroxy, alkoxy, -carbonyl-lower alkyl-heterocycle, -lower alkyl-trimethylsilyl, -lower alkyl-trimethylgermanium or aryloxy. The most preferred analogs of the novel, lactone-stable, "flipped" E-ring camptothecin of the present invention include, but are not limited to: Structure (I)—4R-Ethyl-4-hydroxy-11-(2-(trimethylsilyl)ethyl)-3H-pyrano[2',3':6,7]indolizino[1,2-b]quinoline-2,14-(4H,12H)-dione; Structure (VI)—4R-Ethyl-4-hydroxy-8,9-ethylenedioxy-11-(2-(trimethylgermanyl)ethyl)-3H-pyrano[2',3':6,7]indolizino[1,2-b]quinoline-2,14-(4H,12H)-dione; and Structure (X)—4R-Ethyl-4-hydroxy-8,9-dimethoxy-11-((trimethylsilyl)methylthio)-3H-pyrano[2',3':6,7]indolizino[1,2-b]quinoline-2,14-(4H,12H)-dione.

The novel, lactone-stable, "flipped" E-ring camptothecins of the present invention can be derivatized at the same positions on the A and B rings, as shown above in Structures (I)-(XII). Such derivatization can be for accomplishing any of a number of goals including, but not limited to: (i) increased lipophilicity; (ii) increased stability; (iii) increased interactions with DNA; and the like. Some side-chains on the A and B rings are disclosed in U.S. Pat. Nos. 6,194,579; 5,935,967; 5,674,874; 5,633,260; and 5,900,419 (all of which are incorporated herein by reference in their entirety) and would be suitable for substituent groups on these novel, lactone-stable, "flipped" E-ring camptothecins.
Methods for synthesizing these novel, lactone-stable, "flipped" E-ring camptothecins of the present invention is described below in Scheme I and Scheme II.
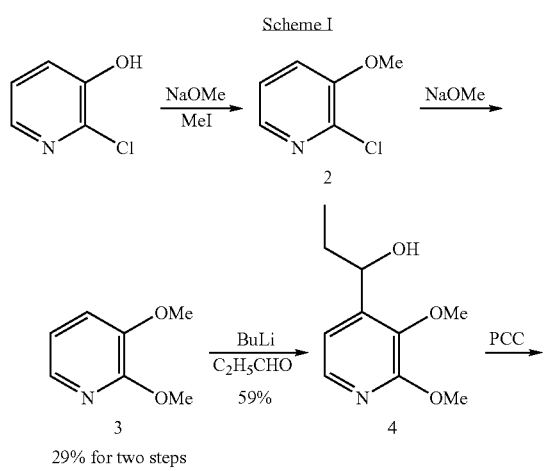
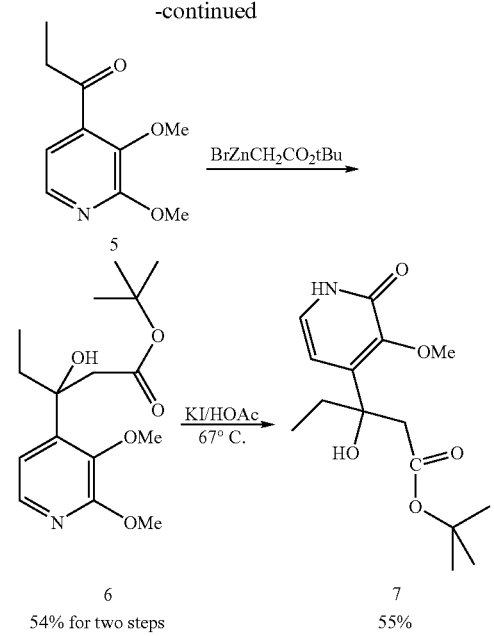

Specific Examples of Experimental Procedures for the Synthesis of "Flipped", Lactone-Stable, E-Ring Camptothecins

I. 2-chloro-3-methoxypyridine (Formula 2)

To a solution of 2-chloro-3-hydroxypyridine (25 g; 193 mmol) in N,N-dimethylformamide (250 mL) was added sodium methoxide (11.5 g; 212 mmol). The mixture was stirred for 4 hours at room temperature and methyl iodide (24 mL; 386 mmol) was added. The resulting mixture was stirred for another 16 hours. The reaction mixture was quenched with water and extracted with dichloromethane. The combined extracts were washed with water, dried over sodium sulfate and concentrated under reduced pressure to provide product (13 g) as a yellow oil. The aforementioned product, 2-chloro-3-methoxypyridine (2), was used for the next step without further purification.

II. 2,3-dimethoxypyridine (Formula 3)

The 2-chloro-3-methoxypyridine (2) (13 g, 90.6 mmol), from Step I, was stirred with 3-equivalents of sodium methoxide (14.7 g, 271.8 mmol) in dimethylformamide (100 mL) at 100° C. until completion of the reaction. The reaction mixture was then quenched with water and extracted with dichloromethane. The combined extracts were washed with water, concentrated and distilled (74° C.; 5 mm Hg) to give the product, 2,3-dimethoxypyridine (3), as a clear oil (7 g; 29% yield for two steps).
$^1$H NMR (300 MHz, CDCl$_3$) δ 7.65 (dd, 1 H, J$_1$=5.1 Hz, J$_2$=1.5 Hz), 6.96 (dd, 1 H, J$_1$=7.5 Hz, J$_2$=1.5 Hz), 6.76 (dd, 1 H, J$_1$=5.1 Hz, J$_2$=7.7 Hz), 3.95 (s, 3 H), 3.80 (s, 3 H).

III. 2,3-dimethoxy-4-(1'-hydroxypropyl)pyridine (Formula 4)

n-Butyllithium (38.7 mL; 10 M in tetrahydrofuran (THF)) was dissolved in THF (600 mL) and cannulated to a solution of 2,3-dimethoxypyridine (3) (22.4 g; 161 mmol) in THF (200 mL) at −78° C. The reaction mixture was then warmed to 0° C. and stirred for 1 hour. The propionaldehyde (29.1 mL; 403 mmol) was added dropwise at −78° C. The reaction mixture was warmed to 25° C. and stirred for 16 hours. The reaction mixture was subsequently quenched with water and extracted with dichloromethane. The combined extracts were dried over sodium sulfate, concentrated under reduced pressure and purified by chromatography (SiO$_2$; 2-10% ethyl acetate/hexane) to give the 2,3-dimethoxy-4-(1'-hydroxypropyl)pyridine (4) product (18.6 g; 59%) as a colorless oil.
$^1$H NMR (300 MHz, CDCl$_3$) δ 7.85 (d, 1 H, J=5.4 Hz), 6.90 (d, 1 H, J=4.8 Hz), 4.92-4.85 (m, 1 H), 4.00 (s, 3 H), 3.86 (s, 3 H), 1.77-1.70 (m, 2 H), 0.95 (t, 3 H, J=7.2 Hz). δ 157.4, 146.1, 140.9, 140.5, 115.0, 70.1, 60.6, 53.7, 30.9, 10.2. Exact mass (m/z, M$^+$) calcd for C$_{10}$H$_{15}$NO$_3$$^+$:197.1056; found 197.1037.

IV. 1-(2,3-dimethoxy-pyridin-4-yl)-propan-1-one (Formula 5)

Celite (27 g, oven dried) and pyridinium chlorochromate (26.46 g; 12.27 mmol) were added to a solution of 2,3-dimethoxy-4-(1'-hydroxypropyl)pyridine (4) (18.6 g; 94.4 mmol) in anhydrous dichloromethane (300 mL). The resultant mixture was stirred at room temperature for 16 hours. The mixture was then filtered through a pad of Celite and silica gel. Concentration generated 13.8 g of the crude 1-(2,3-dimethoxy-pyridin-4-yl)-propan-1-one (5) product which was utilized in the subsequent synthesis step without further purification.
$^1$H NMR (300 MHz, CDCl$_3$) δ 7.84 (d, 1 H, J=5.1 Hz), 6.88 (d, 1 H, J=5.1 Hz), 3.96 (s, 3 H), 3.84 (s, 3 H), 2.89 (q, 2 H, J$_1$=14.4 Hz, J$_2$=7.2Hz), 1.11 (t, 3 H, J=7.2 Hz).

V. 3-(2,3-dimethoxy-pyridin-4-yl)-3-hydroxy-pentanoic acid tert-butyl ester (Formula 6)

To a mixture of zinc (23.1 g; 353.9 mmol) in anhydrous diethyl ether (400 mL) was added trimethylsilyl chloride (0.5 mL). The mixture was stirred for 15 minutes at room temperature and refluxed. Bromoacetic acid tert-butyl ester (56.5 g, 290.0 mmol) was added dropwise and the reaction continued refluxing for an additional 1 hour. The mixture was then cooled to room temperature and cannulated to a solution of 1-(2,3-dimethoxy-pyridin-4-yl)-propan-1-one (13.8 g; 70.8 mmol) in anhydrous tetrahydrofuran (300 mL). The reaction was stirred for 16 hours at room temperature and quenched with saturated ammonium chloride solution. The aqueous layer was extracted with dichloromethane. The combined extracts were dried over sodium sulfate and concentrated under reduced pressure and purified by chromatography (SiO$_2$; 2-10% ethyl acetate/hexane) to give the product 3-(2,3-dimethoxy-pyridin-4-yl)-3-hydroxy-pentanoic acid tert-butyl ester (6) (16.0 g).
$^1$H NMR (300 MHz, CDCl$_3$) δ 7.85 (d, 1 H, J=5.4 Hz), 7.15 (d, 1 H, J=5.1 Hz), 4.62 (s, 1 H), 4.01 (s, 3 H), 3.90 (s, 3 H), 3.16 (d, 1 H, J=15.3 Hz), 2.73 (d, 1 H, J=15.3 Hz), 2.08-1.94 (m, 1 H), 1.92-1.78 (m, 1 H), 1.28 (s, 9 H), 0.77 (t, 3 H, J=7.5 Hz). δ 172.4, 157.6, 145.9, 140.0, 116.4, 81.8, 75.0, 60.1, 53.5, 44.9, 33.0, 27.9, 7.9. Exact mass (m/z, M+Na$^+$) calcd for C$_{16}$H$_{25}$NO$_5$Na$^+$:334.162492, found 334.163420.

VI. 3-hydroxy-3-(3-methoxy-2-oxo-1,2-dihydro-pyridin-4-yl)-pentanoic acid tert-butyl ester (Formula 7)

The mixture of 3-(2,3-dimethoxy-pyridin-4-yl)-3-hydroxy-pentanoic acid tert-butyl ester (6) (3.6 g; 11.56 mmol) and potassium iodide (8 g) in acetic acid (10 mL) was stirred at 60° C. for 16 hours. Reaction was checked by TLC and was not completed. The mixture was then heated at 73° C. for 2 days. The acetic acid was removed by evaporation under reduced pressure and dichloromethane (50 mL) was added. The solution was then washed with saturated sodium bicarbonate solution, dried over sodium sulfate and concentrated under reduced pressure. Purification by column chromatograph over silica gel (10 to 50% ethyl acetate/hexanes) provided 1.9 g of the ester, 3-hydroxy-3-(3-methoxy-2-oxo-1,2-dihydro-pyridin-4-yl)-pentanoic acid tert-butyl ester (7), as a white solid.
$^1$H NMR (300 MHz, CDCl$_3$) δ 7.10 (d, 1 H, J=6.9 Hz), 6.66 (d, 1 H, J=7.2 Hz), 4.68 (s, 1 H), 4.02 (s, 3 H), 3.21 (d, 1 H, J=15.9 Hz), 2.72 (d, 1 H, J=15.9 Hz), 2.04-1.90 (m, 1 H), 1.88-1.78 (m, 1 H), 1.35 (s, 9 H), 0.82 (t, 3 H, J=7.2 Hz). δ 172.6, 161.4, 146.9, 144.5, 127.5, 107.1, 82.0, 74.9, 59.1, 44.5, 32.8, 28.0, 7.8. Exact mass (m/z, M+Na$^+$) calcd for C$_{15}$H$_{23}$NO$_5$Na$^+$: 320.14684, found 320.14556.

VII. 2-chloro-3-hydroxymethylquinoline

To a solution of 2-chloro-3-formylquinoline (6 g; 21.3 mmol) in 150 mL of methanol was added sodium borohydride (1.8 g; 46.97 mmol) and was stirred at room temperature for 16 hours. Methanol was removed by rotary evaporation. The residue was re-suspended in chloroform, washed with water and dried over potassium carbonate. After filtration through a silica gel pad, the product, 2-chloro-3-hydroxymethylquinoline was present as a white solid (4.3 g), which was used for the next synthesis step without further purification.

$^1$H NMR (300 MHz, CDCl$_3$) δ 8.24 (s, 1 H), 7.96 (dd, 1 H, J$_1$=8.4 Hz, J$_2$=0.6 Hz), 7.78 (d, 1 H, J=8.1 Hz), 7.69-7.64 (m, 1 H), 7.54-7.20 (m, 1 H), 4.88 (d, 2 H, J=1.2 Hz).

VIII. 2-iodo-3-iodomethylquinoline (Formula 10)

To a mixture of 2-chloro-3-hydroxymethylquinoline (crude, 4.3 g) and sodium iodide (20 g) in acetonitrile (200 mL) was added chlorotrimethylsilane (16 mL). The resulted mixture was refluxed 6 hours and stirred for two days at room temperature. After concentration, purification by column chromatograph over silica gel (2 to 5% ethyl acetate/hexanes) provided 4.2 g of 2-iodo-3-iodomethylquinoline (10), as a yellow solid.

$^1$H NMR (300 MHz, CDCl$_3$) δ 8.08 (s, 1 H), 7.98 (d, 1 H, J=8.4 Hz), 7.71 (d, 1 H, J=8.1 Hz), 7.68-7.62 (m, 1 H), 7.51 (t, 1 H, J=6.9 Hz), 4.60 (s, 2 H). δ 148.6, 135.9, 135.7, 130.9, 128.8, 127.9, 127.7, 127.5, 124.4, 9.5. Exact mass (m/z, M+H$^+$) calcd for C$_{10}$H$_7$I$_2$NH$^+$: 395.87407, found 395.87441.

IX. 3-[1-(2-iodo-quinolin-3-ylmethyl)-3-methoxy-2-oxo-1,2-dihydro-pyridin-4-yl]-3-hydroxy-pentanoic acid tert-butyl ester (Formula 11)

To an anhydrous 1,2-dimethoxyethane (15 mL) solution of 3-hydroxy-3-(3-methoxy-2-oxo-1,2-dihydro-pyridin-4-yl)-pentanoic acid tert-butyl ester (7) (330 mg; 0.8355 mmol), from Step VI, was added potassium tert-butoxide (0.92 mL; M=1 in tert-butyl alcohol). The white suspension was stirred at room temperature for one hour. Then, the quinoline derivative, 2-iodo-3-iodomethylquinoline (10) (248 mg; 0.8355 mmol) was added. The resulted mixture was stirred at 90° C. for 16 hours. After the mixture was concentrated under reduced pressure to near dryness, the residue was taken up in dichloromethane (20 mL), washed with water, dried over sodium sulfate and concentrated under reduced pressure. Purification by column chromatograph over silica gel (10 to 50% ethyl acetate/hexanes) provided 445 mg of ester (11), as a yellow solid:

$^1$H NMR (300 MHz, CDCl$_3$) δ 8.05 (d, 1 H, J=7.5 Hz), 7.74-7.52 (m, 4 H), 7.18 (d, 1 H, J=7.5 Hz), 6.65 (d, 1 H, J=7.5 Hz), 5.40-5.25 (m, 2 H), 4.65 (s, 1 H), 4.04 (s, 3 H), 3.25 (d, 1 H, J=15.9 Hz), 2.75 (d, 1 H, J=15.9 Hz), 2.04-1.92 (m, 1 H), 1.90-178 (m, 1 H), 1.38 (s, 9 H), 0.86 (t, 3 H, J=7.2 Hz). δ 172.6, 159.0, 148.8, 145.0, 144.5, 135.0, 132.4, 130.5, 130.0, 128.5, 127.7, 127.6, 127.1, 122.8, 106.1, 81.8, 74.6, 59.2, 55.2, 44.3, 32.7, 28.1, 7.9. Exact mass (m/z, M+Na$^+$) calcd for C$_{25}$H$_{29}$IN$_2$O$_5$Na$^+$: 587.101339, found 587.10016.

X. 3-hydroxy-3-(8-methoxy-9-oxo-9,11-dihydro-indolizino[1,2-b]quinolin-7-yl)-pentanoic acid tert-butyl ester (Formula 12)

To an oven-dried high pressure reaction flask was added ester (11) (320 mg; 0.567 mmol), potassium acetate (139 mg, 1.42 mmol) and bis(triphenylphosphine)palladium(II) acetate (21 mg, 0.03 mmol). Anhydrous acetonitrile (7 mL) was added and the reaction mixture was bubble with argon for twenty minutes. The flask was closed and was heated at 100° C. for 16 hours. The reaction was then quenched with 1 N HCl and extracted with dichloromethane. The combined extracts was dried over sodium sulfate and concentrated under reduced pressure. Purification by column chromatograph over silica gel (10 to 50% ethyl acetate/hexanes) provided 120 mg (66% with 85 mg of starting material recovered) of 3-hydroxy-3-(8-methoxy-9-oxo-9,11-dihydro-indolizino[1,2-b]quinolin-7-yl)-pentanoic acid tert-butyl ester (12), as a yellow solid.

$^1$H NMR (300 MHz, CDCl$_3$) δ 8.33 (s, 1 H), 8.21 (d, 1 H, J=8.4 Hz), 7.90 (d, 1 H, J=8.1 Hz), 7.80 (t, 1 H, J=7.5 Hz), 7.76 (s, 1 H), 7.62 (t, 1 H, J=7.5 Hz), 5.28 (s, 2 H), 4.80 (s, 1 H), 4.15 (s, 3 H), 3.32 (d, 1 H, J=15.9 Hz), 2.79 (d, 1 H, J=15.9 Hz), 2.12-1.98 (m, 1 H), 1.92-178 (m, 1 H), 1.34 (s, 9 H), 0.86 (t, 3 H, J=7.5 Hz). MS (m/z, M+1) 437.7

XI. (R/S)-"Flipped", E-ring Camptothecin (FCPT; Generic Structural Formula of the Camptothecin of the Present Invention)

To a solution of 3-hydroxy-3-(8-methoxy-9-oxo-9,11-dihydro-indolizino[1,2-b]quinolin-7-yl)-pentanoic acid tert-butyl ester (12) (100 mg, 0.229 mmol) in dichloromethane (5 mL) was added boron tribromide (1.15 mL, M=1 in dichloromethane) at −78° C. The mixture was stirred at 0° C. for 5 hours, quenched with ice-water. The resulting precipitate was filtered and suspended in 5 mL of water. A 0.2 N sodium hydroxide solution was added until turn homogeneous. Then, 2 mL of hydrogen peroxide (40% in water) was added and the solution was stirred for 16 hours. Subsequently, 37% HCl solution was added until PH reached a value of 1.0. The resulting precipitate was filtered and dried to give 30 mg of intermediate FCPT acid form. The above intermediate (19 mg, 0.052 mmol) was dissolved in anhydrous N,N-dimethylformate (2 mL). 4-dimethylaminopyridine (13 mg, 0.104 mmol) and a solution of dicyclohexylcarbodiimide (0.1 mL, M=1 in dichloromethane) were added and the reaction was stirred for two days. The reaction was quenched with 0.1 mL of acetic acid. After the mixture was concentrated under reduced pressure to near dryness, the residue was purified by column chromatograph over silica gel (10% methanol/dichloromethane) to provide 10 mg of (R/S)-FCPT, as a yellow solid:

$^1$H NMR (300 MHz, CDCl$_3$/CD$_3$OD) δ 8.33 (s, 1 H), 8.02 (d, 1 H, J=8.4 Hz), 7.83 (d, 1 H, J=7.2 Hz), 7.73-7.67 (m, 1 H), 7.55-7.51 (m, 1 H), 7.46 (s, 1 H), 5.19 (s, 2 H), 2.88 (dd, 2 H, J$_1$=15.9 Hz, J$_2$=20.4 Hz), 1.73 (q, 2 H), 0.86 (t, 3 H, J=7.3 Hz). MS (m/z, M+1) 349.6.

Similarly, the novel, lactone-stable, "flipped" E-ring germanium-containing camptothecins of the present invention may be prepared according to the synthetic protocols set forth in Scheme 3 through Scheme 6, below.

Scheme 3

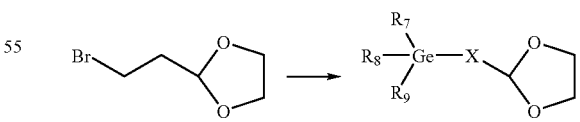

Scheme 3, above, illustrates the synthesis of the dioxolane germanium intermediate analog, which is used in the addition reaction to substitute the germanium-containing moiety onto the camptothecin scaffold. The synthesis is preferably accomplished through a Grignard reaction utilizing a magnesium suspension and halogenated reactants to achieve the desired substitution of the trisubstituted germanium for the corresponding halogen atom (shown in the Scheme as bromine). Reaction specifics of the Grignard conversion are well known, are set forth in the examples below, and are not limitative of the invention.

Scheme 4

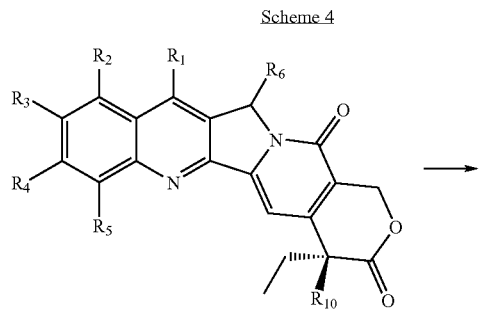

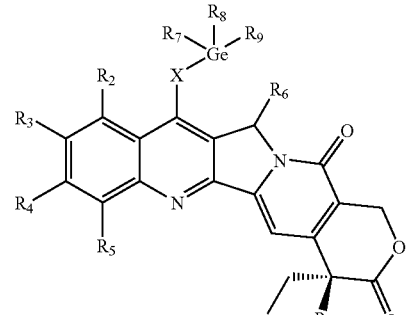

Scheme 4, above, illustrates the substitution of the germanium-containing moiety at C7 of the camptothecin scaffold. The synthetic process for this substitution is similar to that disclosed in U.S. Pat. No. 5,910,491, and others. The final product is formed via a modified Minisci alkylation, specifically, taking camptothecin and reacting it with the chosen intermediate in the presence of a metal sulfate, with slow addition of sulfuric acid and a strong oxidizing agent (hydrogen peroxide is most preferred) to form the germanium-substituted camptothecin as shown.

In the structures shown here and below, "X" refers to a hydrocarbon bridge (alkylene, alkenylene or alkynylene) of from 1 to 6 total carbons, or may be a bond if a direct bond of germanium to the camptothecin scaffold is desired. By varying the hydrocarbon chain length of the intermediate used, the exact length of X may thus be varied. Substitutions at other positions along the camptothecin scaffold may be added before or after the addition of the germanium side-chain.

Scheme 5

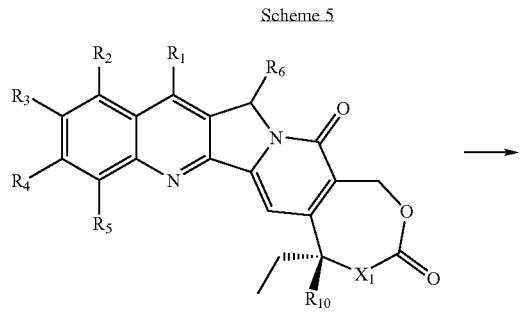

-continued

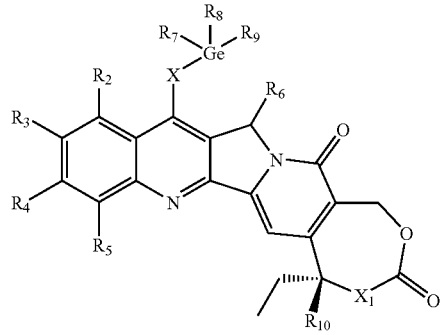

Scheme 5, above, illustrates the synthetic process of making a germanium-containing camptothecin where the E-ring is 7- or 8-membered, as opposed to the naturally-occurring camptothecin E-ring. The process is the same as that for Scheme 2, but with a change in initial reactants. In the preferred analogs made by this Scheme, $X_1$ is —$CH_2$— or —$CH_2CH_2$—.

Scheme 6

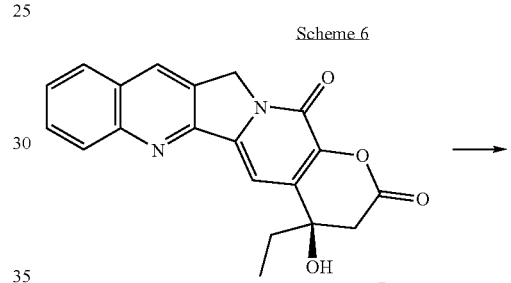

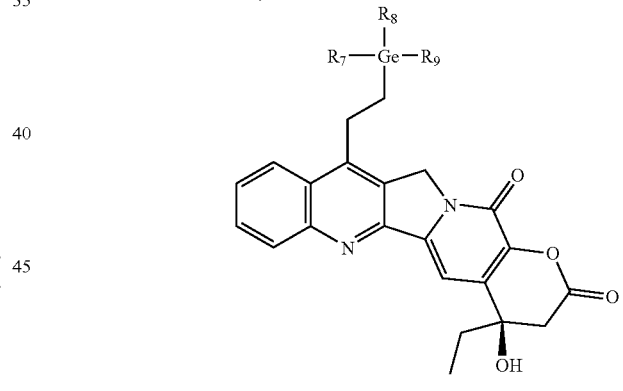

Scheme 6, above, illustrates the synthetic process used to make the most preferred germanium-containing novel, lactone-stable, "flipped" camptothecin analog of the present invention: 4R-Ethyl-4-hydroxy-11-(2-(trimethylgermanyl)ethyl)-3H-pyrano[2',3':6,7]indolizino[1,2-b]quinoline-2,14-(4H,12H)-dione. In this Scheme, and in Schemes 2 and 3, for the preferred analog, $R_7$, $R_8$, and $R_9$ are all methyl, and X is —$CH_2CH_2$—.

Germanium-Containing, "Flipped", Lactone-Stable E-Ring Camptothecins

The following specific examples are illustrative of the synthetic process used to make the germanium-containing, novel, lactone-stable, "flipped" E-ring camptothecins, and analogs thereof, and are not limitative of the present invention.

A. (2-[1,3]dioxolan-2-yl-ethyl)-trimethyl germane

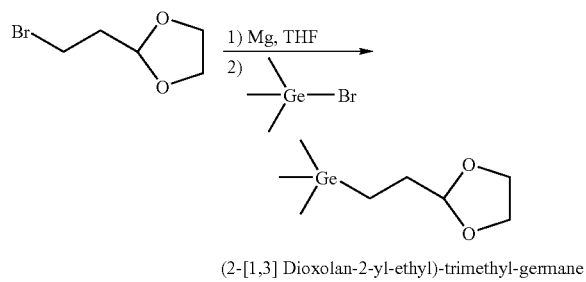

(2-[1,3] Dioxolan-2-yl-ethyl)-trimethyl-germane

To a suspension of magnesium (0.37 g) in tetrahydrofuran (THF) (10 mL) was added 2-(2-bromoethyl)-1,3-dioxolane (2.7 g) at 0° C. The mixture was warmed to room temperature. After the reaction was initiated, the reaction mixture was brought back to 0-5° C. The reaction was continued for 2 hours at 0° C. and 16 hours at room temperature. The reaction was quenched with 10 mL of ice water, extracted with ether (3×10 mL) and concentrated. The crude product was bulb-to-bulb distilled in a Kugelrohr apparatus to give the product, (2-[1,3]dioxolan-2-yl-ethyl)-trimethyl germanium, as a clear oil.

$^1$H NMR (300 MHz, CDCl$_3$) δ 4.76 (1H, t, J=4.8 Hz), 3.77-3.95 (4H, m), 1.57-1.65 (2H, m), 0.67-0.75 (2H, m), 0.058 (9H, s)

B. Proposed Preparation of 7-(2'-trimethylgermanyl) "Flipped" Camptothecin

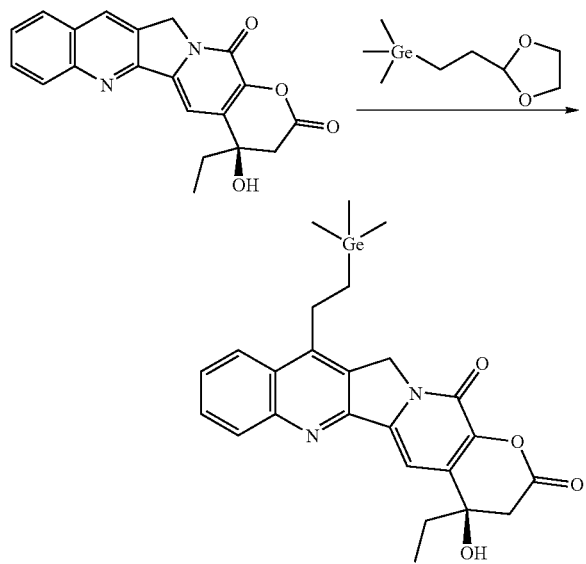

To a suspension of the novel, lactone-stable, "flipped" E-ring camptothecin of the present invention (200 mg) in water (10 mL) and acetic acid (5 mL) will be added FeSO$_4$.17H$_2$O (400 mg). The mixture will be stirred for 10 min at room temperature. (2-[1,3]Dioxolan-2-yl-ethyl)-trimethyl-germane (0.5 mL) will be added and the resultant mixture cooled to 0° C. Concentrated H$_2$SO$_4$ will then be added dropwise followed by 30% H$_2$O$_2$ (0.3 mL). The solution will be stirred at room temperature for 3 hours, with the reaction then being poured into ice. The aqueous phase will be extracted with chloroform (3×20 mL). The combined organic extracts will then be washed with water, dried over anhydrous sodium sulfate, filtrated through silica gel, and concentrated by rotary evaporation. Purification by column chromatography over silica gel (50% Ethyl acetate/hexanes as eluents) will provide the product.

Formulation and Methods of Administration

In addition, to disclosing methods for the synthesis of novel, lactone-stable, "flipped" E-ring camptothecins and their various analogs, the present invention also discloses and claims pharmaceutical formulations which may be utilized with said novel, lactone-stable "flipped" E-ring camptothecins and their various analogs. These formulations are efficacious for use with highly lipophilic analogs such as the novel, lactone-stable, "flipped" E-ring camptothecins of the present invention, and their various analogs, which are even more lipophilic than their 7-member E-ring counterparts (and even greater when they possess a silane or germanyl moiety).

By way of non-limiting example, the novel compositions and formulations of the present invention are adapted for: (i) oral (e.g., tablet, suspension, solution, gelatin capsule (hard or soft), sublingual, dissolvable tablet, troche, and the like), with sublingual administration avoiding first-pass metabolism through the liver; (ii) injection (e.g., subcutaneous administration, intradermal administration, subdermal administration, intramuscular administration, depot administration, intravenous administration, intra-arterial administration, and the like), wherein the administration may occur by, e.g., injection delivery, delivery via parenteral bolus, slow intravenous injection, and intravenous drip, and infusion devices (e.g., implantable infusion devices, both active and passive); (iii) intra-cavitary (e.g., into the intrapleural, intraperitoneal, intravesicular, and/or intrathecal spaces); and (iv) per rectum (e.g., suppository, retention enema) administration routes. The above-mentioned compositions and formulations include as their active ingredient said novel, lactone-stable, "flipped" E-ring camptothecin, pharmaceutically-acceptable salt, and/or an analog thereof, as set forth herein.

Ideal properties of chemotherapeutic formulations include: (i) treatment, mitigation, and/or delay in progression, and/or improved survival of patients with a neoplastic disease; (ii) an acceptably low level of chemotherapy-associated side-effects (with associated treatment interruptions, delays or dose modifications due to such side-effects); (iii) lack of interference with anti-tumor activity of other chemotherapeutic agents (which may be concomitantly administered) and overall lack of untoward drug-drug interactions; (iv) and efficacy in the form of medical benefit to the subject by increasing objective tumor response rate, increasing the time to tumor progression or the duration of tumor remission or disease stabilization, and improving overall patient survival.

A. Parenteral Formulations and Administration

Aspects of the invention include controlled or other doses, dosage forms, formulations, compositions and/or devices containing a novel, lactone-stable, "flipped" E-ring camptothecin of the present invention and/or a derivative thereof, include, but are not limited to, doses and dosage forms for injection, (e.g., subcutaneous administration, subdermal administration, intramuscular administration, depot administration, intravenous administration (including delivery via bolus, slow intravenous injection, intravenous drip), and infusion devices (including implantable infusion devices, both active and passive).

Examples of dosage of forms suitable for injection of the compounds and formulations of the invention include delivery via bolus such as single or multiple administrations by intravenous injection, subcutaneous, subdermal, and intramuscular administration. These forms may be injected using syringes, pens, jet injectors, and internal or external pumps, for example. Needle-less "jet injectors" are also known in the art and utilize a pneumatic "jet" of pressurized air to inject a fine spray of solution into the skin. See, e.g., *Pharmaceutical Dosage Forms: Parenteral Medications, Vol.* 1, *2nd ed.*, Avis, et al., (Eds.), Mercel Dekker, New York, N.Y. (1992).

Infusion pumps, connected by flexible tubing to a catheter, which is inserted into the tissue just below the skin, are also known in the art. The catheter is left in place for several days at a time. The pump is programmed to dispense the necessary amount of solution at the proper times. Examples of implantable infusion devices for compounds, and formulations of the invention include any solid form in which the active agent is encapsulated within or dispersed throughout a biodegradable polymer or synthetic, polymer such as silicone, silicone rubber, silastic, or similar polymer.

Various examples of controlled drug formulations useful for delivery of the compounds and formulations of the invention are found in, e.g., Sweetman, S. C. (Ed.), Martindale. *The Complete Drug Reference, 33rd Edition*, Pharmaceutical Press, Chicago, pp. 2483 (2002); Aulton, M. E. (Ed.), Pharmaceutics. *The Science of Dosage Form Design*. Churchill Livingstone, Edinburgh, pp. 734 pp. (2000); and, Ansel, H. C., et al., *Pharmaceutical Dosage Forms and Drug Delivery Systems, 7th Ed.*, Lippincott pp. 676 (1999). Excipients employed in the manufacture of drug delivery systems are described in various publications known to those skilled in the art including, for example, Kibbe, E. H., *Handbook of Pharmaceutical Excipients, 3rd Ed.*, American Pharmaceutical Association, Washington, pp. 665 pp (2000).

Further examples of dosage forms of the invention include, but are not limited to modified-release (MR) dosage forms including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, however these terms may be applicable to any of the dosage forms, formulations, compositions and/or devices described herein. These formulations effect delayed total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

Modified-release dosage forms of the invention include dosage forms having drug release features based on time, course, and/or location which are designed to accomplish therapeutic or convenience objectives not offered by conventional or immediate-release forms. See, e.g., Bogner, R. H., Bioavailability and bioequivalence of extended-release oral dosage forms. *U.S. Pharmacist* 22(Suppl.):3-12 (1997). Extended-release dosage forms of the invention include, for example, as defined by The United States Food and Drug Administration (FDA), a dosage form that allows a reduction in dosing frequency to that presented by a conventional dosage form, e.g., a solution or an immediate-release dosage form.

The present invention also envisions extended-release formulations containing a novel, lactone-stable, "flipped" E-ring camptothecin of the present invention and/or an analog thereof, for parenteral administration. Extending the rate of release and subsequent pharmacological activity of said novel, lactone-stable, "flipped" E-ring camptothecin, pharmaceutically-acceptable salt, and/or an analog thereof, following injection may be achieved in a number of ways including, but not limited to, crystal or amorphous forms having prolonged dissolution characteristics; slowly dissolving chemical complexes of the camptothecin formulation; solutions or suspensions of said novel, lactone-stable, "flipped" E-ring camptothecin, pharmaceutically-acceptable salt, and/or an analog thereof, in slowly absorbed carriers or vehicles (e.g., as oleaginous); increased particle size of said camptothecin in suspension; or, by injection of slowly eroding microspheres of said novel, lactone-stable, "flipped" E-ring camptothecin, pharmaceutically-acceptable salt, and/or an analog thereof, (see, e.g., Friess, W., et al., Insoluble collagen matrices for prolonged delivery of proteins. *Pharmaceut. Dev. Technol.* 1:185-193 (1996)). For example, the duration of action of the various forms of insulin is based in part on its physical form (amorphous or crystalline), complex formation with added agents, and its dosage form (solution of suspension).

Carriers or excipients can also be used to facilitate administration of the compositions and formulations of the present invention. Examples of carriers and excipients include calcium carbonate, calcium phosphate, various sugars such as lactose, glucose, or sucrose, or types of starch, cellulose derivatives, gelatin, polyethylene glycols and physiologically compatible solvents. It may also be desirable to add suitable dispersing or suspending agents to the pharmaceutical formulation. These may include, for example, aqueous suspensions such as synthetic and natural gums, e.g., tragacanth, acacia, alginate, dextran, sodium carboxymethylcellulose, methylcellulose, polyvinyl-pyrrolidone or gelatin.

It is possible that various other ingredients may also be utilized in the parenteral pharmaceutical formulation of the present invention. Such additional ingredients may include wetting agents, oils (e.g., a vegetable oil such as sesame, peanut or olive), analgesic agents, emulsifiers, antioxidants, bulking agents, tonicity modifiers, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

In addition to the above means of achieving extended drug action, the rate and duration of delivery of said novel, lactone-stable, "flipped" E-ring camptothecin, pharmaceutically-acceptable salt, and/or an analog thereof, may be controlled by, for example by using mechanically controlled drug infusion pumps. The present invention in part provides infusion dose delivery formulations and devices, including but not limited to implantable infusion devices for delivery of compositions and formulations of the invention. Implantable infusion devices may employ inert material such as biodegradable polymers listed above or synthetic silicones, for example, cylastic, silicone rubber or other polymers manufactured by the Dow-Corning Corporation. The polymer may be loaded with the novel, lactone-stable, "flipped" E-ring camptothecin pharmaceutically-acceptable salt, and/or an analog thereof, and any excipients. Implantable infusion devices may also comprise a coating of, or a portion of, a medical device wherein the coating comprises the polymer loaded with the novel, lactone-stable, "flipped" E-ring camptothecin of the present invention, pharmaceutically-acceptable salt, and/or an analog thereof, and any excipients. Such an implantable infusion device may be prepared, e.g., as disclosed in U.S. Pat. No. 6,309,380, by coating the device with an in vivo biocompatible and biodegradable or bioabsorbable or bioerodable liquid or gel solution containing a polymer with the solution comprising a desired dosage amount of the novel, lactone-stable, "flipped" E-ring camptothecin, pharmaceutically-acceptable salt, and/or an analog thereof, and any excipients. The solution is converted to a film adhering to the medical device thereby forming the implantable novel, lactone-stable, "flipped" E-ring camptothecin-deliverable medical device.

An implantable infusion device may also be prepared by the in situ formation of a novel, lactone-stable, "flipped" E-ring camptothecin-containing solid matrix as disclosed in U.S. Pat. No. 6,120,789, herein incorporated in its entirety. Implantable infusion devices may be passive or active. An active implantable infusion device may comprise: (i) a novel, lactone-stable, "flipped" E-ring camptothecin reservoir; (ii) a means of allowing the novel, lactone-stable, "flipped" E-ring camptothecin and/or a derivative thereof to exit said reservoir (e.g., through a semi-permeable membrane); and (iii) a "driving force" to propel the novel, lactone-stable, "flipped" "flipped" E-ring camptothecin and/or a derivative thereof from said reservoir. Such an active implantable infusion device may additionally be activated by an extrinsic signal, such as that disclosed in, e.g., WO 02/45779, wherein the implantable infusion device comprises a system configured to deliver said novel, lactone-stable, "flipped" E-ring camptothecin, pharmaceutically-acceptable salt, and/or an analog thereof, wherein said infusion device comprises an external activation unit which is operable by the user to request activation of the implantable infusion device, including a controller to reject such a request prior to the expiration of a lockout interval. Examples of an active implantable infusion device include implantable drug pumps. Implantable drug pumps include, for example, miniature, computerized, programmable, refillable drug delivery systems with an attached catheter that inserts into a target organ system, usually the spinal cord or a vessel. See, e.g., Medtronic Inc. Publications: UC9603124EN NP-2687, 1997; UC199503941b EN NP-2347 182577-101,2000; UC199801017a EN NP3273a 182600-101, 2000; UC200002512 EN NP4050, 2000; UC199900546bEN NP-3678EN, 2000. Minneapolis, Minn.: Medtronic, Inc (1997-2000). Many pumps have 2 ports—one into which drugs can be injected and the other that is connected directly to the catheter for bolus administration or analysis of fluid from the catheter. Implantable drug infusion pumps (e.g., SynchroMed EL and SynchroMed Programmable Pumps; manufactured by Medtronic) are indicated for long-term intrathecal infusion of morphine sulfate for the treatment of chronic intractable pain; intravascular infusion of floxuridine for treatment of primary or metastatic cancer; intrathecal injection (e.g., baclofen injection) for severe spasticity; long-term epidural infusion of morphine sulfate for treatment of chronic intractable pain; long-term intravascular infusion of doxorubicin, cisplatin, or methotrexate for the treatment or metastatic cancer; and long-term intravenous infusion of clindamycin for the treatment of osteomyelitis. Such pumps may also be used for the long-term infusion of said novel, lactone-stable, "flipped" E-ring camptothecin, pharmaceutically-acceptable salt, and/or an analog thereof, either at a desired concentration, for a desired number of doses, or steady-state administration. One form of a typical implantable drug infusion pump (e.g., SynchroMed EL Programmable Pump; Medtronic) is titanium covered and roughly disk shaped (measuring 85.2 mm in diameter, 22.86 mm in thickness and weighing a total of 185 grams), has a drug reservoir which holds a total liquid volume of 10 mL, and runs on a lithium thionyl-chloride battery with a 6- to 7-year life, depending upon amount of use. The downloadable memory contains programmed drug delivery parameters and calculated amount of drug remaining, which can be compared with actual amount of drug remaining to access accuracy of pump function, but actual pump function over time is not recorded. The pump is usually implanted in the right or left abdominal wall. Other pumps useful in the invention include, for example, portable disposable infuser pumps (PDIPs). Additionally, implantable infusion devices may employ liposome delivery systems, such as a small unilamellar vesicles, large unilamellar vesicles, and multilamellar vesicles can be formed from a variety of phospholipids, such as cholesterol, stearyl amine or phosphatidylcholines.

The present invention also provides in part dose delivery formulations and devices formulated to enhance bioavailability of said novel, lactone-stable, "flipped" E-ring camptothecin, pharmaceutically-acceptable salt, and/or an analog thereof. This may be in addition to or in combination with any of the formulations or devices described above. An increase in bioavailability of said novel, lactone-stable, "flipped" E-ring camptothecin, pharmaceutically-acceptable salt, and/or an analog thereof, may be achieved by complexation of said novel camptothecin with one or more bioavailability or absorption enhancing agents or in bioavailability or absorption enhancing formulations.

The present invention in part also provides for the formulation of said novel, lactone-stable, "flipped" E-ring camptothecin, pharmaceutically-acceptable salt, and/or an analog thereof, in a microemulsion to enhance bioavailability. A microemulsion is a fluid and stable homogeneous solution composed of four major constituents, comprising: (i) a hydrophilic phase; (ii) a lipophilic phase; (iii) at least one surfactant (SA) and (iv) at least one cosurfactant (CoSA). A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution. Examples of suitable surfactants include mono-, di- and triglycerides and polyethylene glycol (PEG) mono- and diesters. A cosurfactant, also known as a "co-surface-active agent", is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

In the preferred formulation of the present invention, the HLCD is a C7-substituted camptothecin analog; with the most preferred HLCDs including, but not limited to, a novel, lactone-stable, "flipped" E-ring camptothecin with silyl-side chain or a novel, lactone-stable, "flipped" E-ring camptothecin with germanium-containing side chain.

The preferred solvents include N-methylpyrrolidinone (NMP), dimethylacetamide (DMA), and/or dimethylisosorbide (DMI); or a combination of two or more of the aforementioned solvents being utilized as co-solvents. The most preferred solvent is NMP, a combination of NMP and DMA as co-solvents, or DMA as the primary co-solvent.

Preferred surfactants include, but are not limited to, polysorbates; with the most preferred surfactant being polysorbate 80. Preferred alcohols include, but are not limited to, ethyl alcohol and benzyl alcohol; with the most preferred alcohol being denatured ethyl alcohol. The preferred low molecular weight polyethylene glycols (PEGs), include but are not limited to, PEG 100, PEG 200, PEG 300, PEG 400, PEG 600, PEG 800; with the most preferred PEG being PEG 300.

A preferred embodiment of the present invention is a formulation comprising said novel, lactone-stable, "flipped" E-ring camptothecin, pharmaceutically-acceptable salt, and/or an analog thereof, dissolved in N-methylpyrrolidinone (NMP), or dimethylisosorbide (DMI) and/or dimethylacetamide (DMA), alone or in combination, in the presence of a pharmaceutically-acceptable acid. An additional embodiment of the claimed invention is where the pharmaceutically-acceptable acid is an organic carboxylic acid, with the most preferred being citric acid. In another embodiment of the claimed invention, the solution of said novel, lactone-stable, "flipped" E-ring camptothecin, pharmaceutically-acceptable salt, and/or an analog thereof, contains from about 0.1 mg to about 100 mg of the novel, lactone-stable, "flipped" E-ring camptothecin, pharmaceutically-acceptable salt, and/or analogs thereof, per mL of solution. This concentration would be effective for both oral and parenteral administration of said novel, lactone-stable, "flipped" E-ring camptothecin, pharmaceutically-acceptable salt, and/or an analog thereof.

The novel, lactone-stable, "flipped" E-ring camptothecin solution is prepared by dissolving the desired components in N-methylpyrrolidinone (NMP), dimethylisosorbide (DMI) and/or dimethylacetamide (DMA). Dimethylisosorbide has been used as solvent for muscle relaxants (see, e.g., U.S. Pat. No. 3,699,230), tetracyclines (U.S. Pat. No. 3,219,529), aspirin (U.S. Pat. No. 4,228,162), and steroids (U.S. Pat. No. 4,082,881). NMP, DMI, and DMA have very good toxicity profiles and are miscible with ethanol, propylene glycol, isopropyl myristate, water, diethyl ether, corn oil, acetone, cottonseed oil, and the like.

The present invention is prepared by dissolving the desired components in NMP, DMI and/or DMA and the resulting solution is then filtered and the filtrate collected. The amount of the novel, lactone-stable, "flipped" E-ring camptothecin contained in the solution of this invention is not specifically restricted but may be any amount convenient for pharmaceutical purposes, and may be selected according to the dosage to be prepared. A preferred capsule filling solution contains a sufficient concentration of said novel, lactone-stable, "flipped" E-ring camptothecin, pharmaceutically-acceptable salt, and/or an analog thereof, so as to provide a total dose of about 0.1 mg/m$^2$ to 100 mg/m$^2$.

As a preferred embodiment of the claimed invention, the novel, lactone-stable, "flipped" E-ring camptothecin solution is prepared by dissolving the desired components in N-methylpyrrolidinone (NMP), dimethylisosorbide (DMI) and/or dimethylacetamide (DMA) in the presence of a pharmaceutically-acceptable acid. As previously defined, a pharmaceutically-acceptable acid is included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred, as well as phosphoric acid. The amount of acid used may be from about 0.005 to about 0.5 parts by weight of acid per part by weight of said novel, lactone-stable, "flipped" E-ring camptothecin, pharmaceutically-acceptable salt, and/or an analog thereof, and preferably from about 0.01 to 0.3 part by weight of acid per part by weight of said novel, lactone-stable, "flipped" E-ring camptothecin, pharmaceutically-acceptable salt, and/or an analog thereof. Citric acid is preferably used in a proportion of from about 0.05 to about 0.1, and about 0.1 part by weight in the presence of taurocholic acid or a pharmaceutically-acceptable salt thereof.

In the formulations provided by the instant invention, the said novel, lactone-stable, "flipped" E-ring camptothecin, pharmaceutically-acceptable salt, and/or an analog thereof, is both soluble and maintained in its active "closed" lactone-stable form. The non-enzymatic conversion of the pH labile E-ring from the "closed" lactone (i.e., active) to the "open" carboxylate form (i.e., inactive) is reduced by formulating the novel, "flipped" lactone-stable, E-ring camptothecin under acidic pH conditions (<5.0). Thus, a water soluble acid is included to assure that an acidic pH value is maintained upon dilution to form the micellar solution. Examples of preferred solid water-soluble organic carboxylic acids effective in the present invention include, but are not limited to, citric, gluconic, maleic, tartaric, or ascorbic acids. Other acids may be also employed, but citric and phosphoric acid are most preferred.

One embodiment of the present invention is a method of administration of the novel, lactone-stable, "flipped" E-ring camptothecin to a patient with cancer comprising infusing a fixed amount of said novel, lactone-stable, "flipped" E-ring camptothecin, pharmaceutically-acceptable salt, and/or an analog thereof, over a period of time and repeated at predetermined intervals.

Another embodiment of the invention discloses the administration of a formulation which contains a total dose of approximately 0.1 mg/m$^2$ to approximately 100 mg/m$^2$ of said novel, lactone-stable, "flipped" E-ring camptothecin, pharmaceutically-acceptable salt, and/or analog thereof. In a preferred embodiment, the camptothecin is dissolved, in the presence of a pharmaceutically-acceptable acid, in one or more solvents including, but not limited to, N-methylpyrrolidinone, dimethylisosorbide, or dimethylacetamide.

One embodiment discloses a formulation comprising a total does of approximately 0.1 mg/m$^2$ to approximately 100 mg/m$^2$ of said novel, lactone-stable, "flipped" E-ring camptothecin, pharmaceutically-acceptable salt, and/or analog thereof, and containing and from approximately 0.01 to approximately 0.9 part by weight of a pharmaceutically-acceptable organic carboxylic acid per part by weight of said lactone-stable, E-ring camptothecin analog, pharmaceutically-acceptable salt, and/or analog thereof. In the most preferred embodiment the pharmaceutically-acceptable organic carboxylic acid is citric acid.

One embodiment of the present invention discloses a formulation comprising a pharmaceutically-acceptable organic carboxylic acid which is from approximately 0.05 to approximately 0.1 part by weight of said novel, lactone-stable, "flipped" E-ring camptothecin analog, pharmaceutically-acceptable salt, and/or analog thereof.

One embodiment discloses a formulation further comprising taurocholic acid, or a pharmaceutically-acceptable salt thereof, and polyethylene glycol.

Another embodiment discloses a formulation comprising for each part by weight of said novel, lactone-stable, "flipped" E-ring camptothecin, pharmaceutically-acceptable salt, and/or analog thereof, approximately 1 to approximately 10 parts by weight of N-methylpyrrolidinone, dimethylisosorbide, or dimethylacetamide, approximately 0.005 to approximately 0.5 parts by weight of citric acid, approximately 1 to approximately 10 parts by weight of taurocholic acid, or a pharmaceutically-acceptable salt thereof, and approximately 1 to approximately 10 parts by weight of polyethylene glycol.

Another embodiment discloses a formulation comprising for each part by weight of said novel, lactone-stable, "flipped"

E-ring camptothecin, pharmaceutically-acceptable salt, and/or analog thereof, approximately 1 to approximately 10 parts by weight of N-methylpyrrolidinone, dimethylisosorbide, or dimethylacetamide, approximately 0.005 to approximately 0.5 parts by weight of a pharmaceutically-acceptable organic carboxylic acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer. In a preferred embodiment, the pharmaceutically-acceptable organic carboxylic acid is citric acid, the polyethylene glycol has a molecular weight of approximately 300.

Another embodiment discloses a formulation comprising at total does of approximately 0.1 mg/m$^2$ to approximately 100 mg/m$^2$ of said novel, lactone-stable, "flipped" E-ring camptothecin analog, pharmaceutically-acceptable salt, and/or analog thereof, dissolved in approximately 1 to approximately 10 parts by weight of N-methylpyrrolidinone, dimethylisosorbide, or dimethylacetamide, in the presence of approximately 0.1 to approximately 0.5 parts by weight of a pharmaceutically-acceptable organic carboxylic acid, wherein said composition further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. In a preferred embodiment, the pharmaceutically-acceptable organic acid is citric or phosphoric acid, the polyethylene glycol has a molecular weight of approximately 300, the lower alcohol is ethanol, and wherein said surfactant is polysorbate-80 or poloxamer PF-127.

Another embodiment of the invention discloses a method where said novel, lactone-stable, "flipped" E-ring camptothecin, pharmaceutically-acceptable salt, and/or an analog thereof, is infused into a patient with cancer, wherein said novel, lactone-stable, "flipped" E-ring camptothecin, pharmaceutically-acceptable salt, and/or an analog thereof, is dissolved in N-methylpyrrolidinone (NMP) in the presence of a pharmaceutically-acceptable acid, said novel, lactone-stable, "flipped" E-ring camptothecin, pharmaceutically-acceptable salt, and/or an analog thereof, is dissolved in dimethylisosorbide (DMI) in the presence of a pharmaceutically-acceptable acid, said novel, lactone-stable, "flipped" E-ring camptothecin, pharmaceutically-acceptable salt, and/or an analog thereof, is dissolved in dimethylacetamide (DMA) in the presence of a pharmaceutically-acceptable acid. An object of the present invention is to provide a solution of the novel, lactone-stable, "flipped" E-ring camptothecin in a NMP-, DMI- and/or DMA-containing solution. It should be noted that the solution may be formulated for parenteral use providing a useful and practical means to dissolve the drug or, as a concentrated solution, useful as a filling solution for oral gelatin capsules or rectal suppositories.

A preferred embodiment of the present invention is an formulation comprising a solution of said novel, lactone-stable, "flipped" E-ring camptothecin dissolved in N-methylpyrrolidinone (NMP), dimethylisosorbide and/or dimethylacetamide containing a sufficient concentration of the novel, lactone-stable, "flipped" E-ring camptothecin to provide a total dosage of about 0.1 mg/m$^2$ to about 100 mg/m$^2$ and containing from about 0.01 to about 0.9 part by weight of a pharmaceutically-acceptable organic carboxylic acid per part by weight of the novel, lactone-stable, "flipped" E-ring camptothecin. The present inventors prefer to use approximately 0.01 to approximately 0.2 part by weight of a pharmaceutically-acceptable organic carboxylic acid per part by weight of the novel, lactone-stable, "flipped" E-ring camptothecin.

An additional embodiment of the present invention is wherein said part by weight of the pharmaceutically-acceptable organic carboxylic acid is from approximately 0.05 to approximately 0.1 part by weight per part by weight of the novel, lactone-stable, "flipped" E-ring camptothecin and the acid is citric acid.

Another embodiment of the invention is an formulation comprising a solution of the novel, lactone-stable, "flipped" E-ring camptothecin dissolved in N-methylpyrrolidinone, dimethylisosorbide and/or dimethylacetamide in the presence of a pharmaceutically-acceptable acid, wherein said solution further comprises taurocholic acid or a pharmaceutically-acceptable salt thereof, and polyethylene glycol.

Yet another embodiment of the present invention is wherein the solution of formulation contains for each part by weight of the novel, lactone-stable, "flipped" E-ring camptothecin, approximately 1 to approximately 10 parts by weight of N-methylpyrrolidinone, dimethylisosorbide and/or dimethylacetamide, approximately 0.005 to approximately 0.5 parts by weight of a pharmaceutically-acceptable acid, approximately 1 to approximately 10 parts by weight of taurocholic acid or a pharmaceutically-acceptable salt thereof, and approximately 1 to approximately 10 parts by weight of polyethylene glycol. An additional embodiment is wherein said acid is an organic carboxylic acid, most preferably citric acid, or phosphoric acid.

Another embodiment of the claimed invention is the formulation further comprises a lower alcohol. Many different alcohols would be effective in the present invention, but most preferably, ethanol. Another embodiment of the claimed invention is the formulation further comprises glycerin as a co-solvent.

Yet another embodiment of the invention is an formulation comprising a solution of the novel, lactone-stable, "flipped" E-ring camptothecin dissolved in N-methylpyrrolidinone, dimethylisosorbide and/or dimethylacetamide in the presence of a pharmaceutically-acceptable acid, wherein said solution further comprises taurocholic acid or a pharmaceutically -acceptable salt thereof, polyethylene glycol, ethanol, glycerin, and a buffer, such as sodium acetate, to maintain an acidic pH.

An additional embodiment of the present invention is wherein said solution contains for each part by weight of the novel, lactone-stable, "flipped" E-ring camptothecin, approximately 1 to approximately 10 parts by weight of N-methylpyrrolidinone, dimethylisosorbide and/or dimethylacetamide, approximately 0.005 to approximately 0.5 parts by weight of a pharmaceutically-acceptable acid, approximately 1 to approximately 10 parts by weight of taurocholic acid, or a pharmaceutically-acceptable salt thereof, approximately 1 to approximately 10 parts by weight of polyethylene glycol, approximately 0.1 to approximately 2 parts by weight of glycerin, approximately 0.1 to approximately 2 parts by weight of ethanol, and approximately 0.005 to approximately 0.5 parts of a buffer.

Another embodiment of the invention is wherein said polyethylene glycol has a molecular weight of about 300, and the formulation further comprises a non-ionic surfactant. Many different surfactants would be effective in the present invention, the poloxamer, PF-127, is most preferred.

Yet another embodiment of the invention is an formulation comprising a solution of the novel, lactone-stable, "flipped" E-ring camptothecin dissolved in dimethylisosorbide or dimethylacetamide in the presence of a pharmaceutically-acceptable acid, wherein said solution further comprises a lower alcohol, polyethylene glycol, and surfactant. As a more preferred embodiment for this formulation, the pharmaceutically-acceptable organic acid is citric acid, the polyethylene glycol has a molecular weight of about 300, the lower alcohol is ethanol and the surfactant is polysorbate-80.

Yet another embodiment of the invention is an formulation comprising a solution providing a total dose of approximately 0.1 mg/m$^2$ to approximately 100 mg/m$^2$ of the novel, lactone-stable, "flipped" E-ring camptothecin dissolved in approximately 1 to approximately 10 parts by weight of N-methylpyrrolidinone, dimethylisosorbide and/or dimethylacetamide in the presence of approximately 0.1 to 0.5 parts by weight of a pharmaceutically-acceptable organic carboxylic acid. This formulation further comprises approximately 5 to approximately 9 parts by weight of polyethylene glycol, approximately 0.1 to approximately 2.0 parts by weight of a pharmaceutically-acceptable alcohol, and approximately 1 to approximately 10 parts by weight of a non-ionic surfactant. More preferred for this aforementioned formulation is when the acid is citric acid, the polyethylene glycol has a molecular weight of about 300, the alcohol is ethanol, and the surfactant is polysorbate-80.

Another embodiment of this invention is an formulation comprising a solution providing a total dose of approximately 0.1 mg/m$^2$ to approximately 100 mg/m$^2$ of the novel, lactone-stable, "flipped" E-ring camptothecin dissolved in approximately 1 to approximately 10 parts by weight of N-methylpyrrolidinone, dimethylisosorbide and/or dimethylacetamide in the presence of approximately 0.1 to approximately 0.5 parts by weight of a pharmaceutically-acceptable organic carboxylic acid. This solution further comprises approximately 0.1 to approximately 2.0 parts by weight of a pharmaceutically-acceptable alcohol, and approximately 1 to approximately 10 parts by weight of a non-ionic surfactant. More specifically, for this formulation, the acid is citric or phosphoric acid, the alcohol is ethanol, and the non-ionic surfactant is comprised of polyoxyethylated castor oil.

Another embodiment of the present invention is an formulation comprising a solution providing a total dose of approximately 0.1 mg/m$^2$ to approximately 100 mg/m$^2$ of the novel, lactone-stable, "flipped" E-ring camptothecin dissolved in approximately 1 to approximately 10 parts by weight of N-methylpyrrolidinone, dimethylisosorbide and/or dimethylacetamide, wherein this solution further comprises approximately 1 to approximately 10 parts by weight polyoxyethylated castor oil, approximately 0.1 to approximately 2 parts by weight dehydrated ethyl alcohol USP, and approximately 0.1 to approximately 0.9 parts by weight citric acid.

In a preferred parenteral formulation, the novel, lactone-stable, "flipped" E-ring camptothecin is solubilized in a manner suitable for clinical use by forming a sterile, nonaqueous solution of 1 part of said novel, lactone-stable, "flipped" E-ring camptothecin, pharmaceutically-acceptable salt, and/or an analog thereof, per 1 to 2 mL in a vehicle comprising dehydrated ethyl alcohol 0.1-2.0 parts by weight, benzyl alcohol 0.1-2.0 parts by weight, citric acid 0.1-0.9 parts by weight, polyethylene glycol (molecular weight 200-300) 4 to 10 parts by weight, polysorbate-80 (Tween 80) 1 to 10 parts, and dimethylisosorbide 1 to 10 parts by weight, contained within an acidified medium with an overall pH of approximately 3 to 4.

Another preferred parenteral formulation comprises the novel, lactone-stable, "flipped" E-ring camptothecin formulated for dilution prior to parenteral administration providing a total dose of approximately 0.1 mg/m$^2$ to 100 mg/m$^2$ of said novel, lactone-stable, "flipped" E-ring camptothecin, pharmaceutically-acceptable salt, and/or an analog thereof, per 2 mL of nonaqueous solvents including, but not limited to, 1 to 10 parts by weight Cremaphor EL™ (polyoxyethylated castor oil), 0.1 to 2 parts by weight dehydrated ethyl alcohol USP, dimethylisosorbide 1 to 10 parts by weight, and citric acid 0.1-0.9 parts by weight to adjust the final pH to between approximately 3 to 4.

One embodiment of the present invention is a method for administration of said novel, lactone-stable, "flipped" E-ring camptothecin, pharmaceutically-acceptable salt, and/or an analog thereof, to a patient with cancer comprising infusing from about 0.1 mg/m$^2$ to about 100 mg/m$^2$ of the novel, lactone-stable, "flipped" E-ring camptothecin, wherein the selected dose is administered at least once over approximately 24 hours and repeated for at least two consecutive days, dependant upon the condition of the patient and the type of cancer or cancers effecting said patient.

Yet another embodiment of the present invention discloses a method for administration of said novel, lactone-stable, "flipped" E-ring camptothecin, pharmaceutically-acceptable salt, and/or an analog thereof, to a patient with cancer comprising continuously infusing from about 0.1 mg/m$^2$ to about 100 mg/m$^2$ of said novel, lactone-stable, "flipped" E-ring camptothecin, pharmaceutically-acceptable salt, and/or an analog thereof, over a duration of approximately 24 to 120 hours every 21 to 28 days.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 100 mg/m$^2$ of said composition over a duration of approximately 120 minutes, given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 75 mg/m$^2$ of said composition over a duration of approximately 120 minutes, given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the administration of a formulation comprising said novel, lactone-stable, "flipped" camptothecin, pharmaceutically-acceptable salt, and/or analog thereof, to a previously untreated patient with cancer, comprising of infusing from approximately 0.1 mg/m$^2$ to approximately 50 mg/m$^2$ of said composition over a duration of approximately 120 minutes, given once per week for three consecutive weeks with 2 weeks rest after each 3 week cycle, wherein said composition is sterilized and prepared for oral, intrapleural, intrathecal, intracisternal, intravesicular, intraperitoneal, topical or parenteral administration to a patient with cancer.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m² to approximately 100 mg/m² of said composition over a duration of approximately 120 minutes every 21 to 28 days.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m² to approximately 75 mg/m² of said composition over a duration of approximately 120 minutes every 21 to 28 days.

One embodiment discloses a method for the parenteral administration of a formulation comprising said novel, lactone-stable, "flipped" camptothecin, pharmaceutically-acceptable salt, and/or analog thereof, to a patient with cancer, said method consisting of infusing from approximately 0.1 mg/m² to approximately 50 mg/m² of said composition over a duration of approximately 120 minutes for three consecutive days every 21 to 28 days.

In one embodiment of the present invention the method is carried out to treat cancer in a subject. In another embodiment the subject is a human with cancer, wherein said cancer includes, as non-limiting examples, one or more cancers of the ovary, breast, lung, esophagus, bladder, stomach, pancreas, liver, testicular, head, neck, oral mucosa, colorectal, anus, kidney, bladder, uroepithelium, lymphoma, central nervous system, prostate, endometrium, uterine, fallopian tube, mesothelioma, peripheral nervous system, melanoma, myeloma, leukemia, and Kaposi's sarcoma. It should be noted that both the site and type of tumor to be treated will, in many cases, influence the preferred route of administration and therapeutic regimen to be applied. Consequently, although the disclosed formulations of the present invention may be most usually administered by intravenous injection or infusion, they also can be delivered directly into the tumor site or by other methods designed to target the drug directly to the tumor site. For example, in patients with malignant pleural effusion, the intrapleural route may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also provided for use where suitable.

Thus, an additional embodiment of the present invention is a solution comprising the novel, lactone-stable, "flipped" E-ring camptothecin dissolved in N-methylpyrrolidinone, dimethylisosorbide and/or dimethylacetamide, in the presence of a pharmaceutically-acceptable acid and this solution is sterilized and prepared for oral, intrapleural, intrathecal, subcutaneous, intracisternal, intravesicular, intraperitoneal, topical or parenteral administration to a patient with cancer.

The disclosed formulations of the present invention may also be utilized in conjunction with one or more other chemotherapeutic agents in methods of convergent therapy whereupon an additional drug or drugs are co-administered along with the claimed composition. Thus, the novel, lactone-stable, "flipped" E-ring camptothecin may be co-administered with numerous other chemotherapeutic agents including, but not limited to: a fluropyrimidine; a pyrimidine nucleoside; a purine nucleoside; an antifolate, a platinum analog; an anthracycline/anthracenedione; an epipodopodophyllotoxin; a camptothecin; a hormone, a hormonal analog; an antihormonal; an enzyme, protein, peptide, or antibody; a vinca alkaloid; a taxane; an epothilone; an antimicrotubule agent; an alkylating agent; an antimetabolite; a topoisomerase inhibitor; an antiviral; or a cytostatic agent. Fluropyrimidines include, for example, 5-fluorouracil [5-FU], S-1 capecitabine, ftorafur, 5'deoxyflurouridine, UFT, eniluracil, and the like. Pyrimidine nucleosides include, for example, cytarabine, deoxycytidine, 5-azacytosine, gemcitabine, 5-azadeoxycytidine, and the like. Purine nucleosides include, for example, fludarabine, 6-mercaptopurine, thioguanine, allopurinol, cladribine, 2-chloro adenosine. Anti-folates include, for example, methotrexate (MTX), trimetrexate, aminopterin, and methylene-10-deazaaminopterin (MDAM). Platinum analogs include, for example, cisplatin, carboplatin, oxaplatin, picoplatin, tetraplatin, platinum-DACH and analogs thereof. Anthracyclines/anthracenediones include, for example, doxorubicin, daunorubicin, epirubicin, and idarubicin. Epipodophyllotoxin derivatives include, for example, etoposide, etoposide phosphate and teniposide. Camptothecins include, for example, irinotecan, topotecan, 9-aminocamptothecin, 10,11-methylenedioxy-camptothecin, karenitecin, 9-nitrocamtothecin, and TAS 103. Hormones and hormonal analogs may include, for example, estrogens and estrogen analogs, including anastrazole, diethylstilbesterol, estradiol, premarin, raloxifene; progesterone, progesterone analogs and progestins, including progesterone, norethynodrel, esthisterone, dimesthisterone, megestrol acetate, medroxyprogesterone acetate, hydroxyprogesterone caproate, and norethisterone; androgens, including fluoxymesterone, methyltestosterone and testosterone; adrenocorticosteroids, including dexamthasone. Antihormones include, for example, antiestrogens, including, tamoxifen, fulvestrant, toremifene; aminoglutethimide, testolactone, droloxifene, anastrozole; antiandrogens, including, bicalutamide, flutamide, nilutamide, goserelin; antitestosterones, including flutamide, leuprolide, triptorelin; adrenal steroid inhibitors including, aminoglutethimide and mitotane; and anti-leuteinizing, including goserelin. Enzymes, proteins, peptides and antibodies include, for example, asparaginase, cetuximab, erlotinib, bevacizumab, rituximab, gefitinib, trastuzumab, interleukins, interferons, leuprolide, pegasparanase, and the like. Vinca Alkaloids include, for example, vincristine, vinblastine, vinorelbine, vindesine, and like. Taxanes include, for example, paclitaxel, docetaxel, and formulations and analogs thereof. Alkylating agents may include, for example, dacarbazine; procarbazine; temozolamide; thiotepa; nitrogen mustards (e.g., mechlorethamine, chlorambucil, L-phenylalanine mustard, melphelan, and the like); oxazaphosphorines (e.g., ifosphamide, cyclophosphamide, mefosphamide, perfosfamide, trophosphamide and the like); alkyl sulfonates (e.g., busulfan); and nitrosoureas (e.g., carmustine, lomustine, semustine and the like). Epothilones include, for example, epothilones A-E. Antimetabolites include, for example, tomudex and methotrexate, 6-mercaptopurine, 6-thioguanine. Topoisomerase inhibitors include, for example, irinotecan, and topotecan, karenitecin, amsacrine, etoposide, etoposide phosphate, teniposide, and doxorubicin, daunorubicin, and other analogs. Antiviral agents include, for example, acyclovir, valacyclovir, ganciclovir, amantadine, rimantadine, lamivudine, and zidovudine. Cytostatic agents include, for example, bevacizumab, trastuzumab, rituximab, and the like, as well as growth inhibitors such as erlotinib, and the like. In general, cytostatic agents are mechanism-based agents that slow the progression of neoplastic disease.

The novel, lactone-stable, "flipped" E-ring camptothecin of the present invention in N-methylpyrrolidinone, dimethylisosorbide and/or dimethylacetamide when administered parenterally, is preferably diluted with an appropriate volume of a parenteral vehicle to a concentration so a to provide a total dose of approximately 0.1 mg/m$^2$ to approximately 100 mg/m$^2$ of the novel, lactone-stable, "flipped" E-ring camptothecin activity. A further embodiment of the claimed invention is a sterile solution of any of the claimed the novel, lactone-stable, "flipped" E-ring camptothecin compositions and formulations for sterile administration to a patient with cancer upon dilution with a sterile parenteral vehicle. For the purposes of the present invention, parenteral vehicles include dextrose approximately 5% to approximately 10% in water, approximately 0.9% NaCl in water (with or without 5% or 10% Dextrose), approximately 0.45% NaCl in water (with or without 5% or 10% Dextrose), and approximately 3% NaCl in water (with or without 5% to 10% Dextrose), or sterile lipid formulations, such as intralipid, used for parenteral nutritional support for cancer patients.

Clinicians will administer said novel, lactone-stable, "flipped" E-ring camptothecin, pharmaceutically-acceptable salt, and/or an analog thereof, to human patients with cancer according to schedules that maximize its potential chemotherapeutic effects and diminish its potential toxic side effects. Except at extremely high doses which produce high plasma concentrations of the drugs, the chemotherapeutic activity of said novel, lactone-stable, "flipped" E-ring camptothecin, pharmaceutically-acceptable salt, and/or an analog thereof, can be increased by increasing the duration of exposure (i.e., time dependent) rather than increasing the dose (i.e., dose dependent) of the drug. The greater chemotherapeutic effects associated with increasing the duration of exposure is a finding that is most likely related to the predominant S-phase mode of chemotherapeutic activity of said novel, lactone-stable, "flipped" E-ring camptothecin, pharmaceutically-acceptable salt, and/or an analog thereof. The novel, lactone-stable, "flipped" E-ring camptothecin, pharmaceutically-acceptable salt, and/or an analog thereof, is an S-phase-active agent; therefore, the greatest chemotherapeutic effect in humans will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

B. Oral and Rectal Formulations and Administration

Oral formulations include tablets, suspensions, solutions, gelatin capsules (hard or soft), dissolvable tablets, troche, and the like. It should be noted that with sublingual administration, first-pass metabolism through the liver (i.e., the cytochrome $P_{450}$ oxidase system) is avoided The above-mentioned compositions and formulations include as their active ingredient said novel, lactone-stable, "flipped" E-ring camptothecin, pharmaceutically-acceptable salt, and/or an analog thereof, as set forth herein. Highly Lipophilic Camptothecin Analogs (HLCDs), as that term is recognized within the art, are defined as having a water solubility of less than 5 μg/mL of water.

When oral dosages are to be administered in a capsule form, it is clearly superior to have a concentrated solution of the novel, lactone-stable, "flipped" E-ring camptothecin suitable for encapsulation within a soft or hard gelatin capsule. Concentrated solutions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance in the intestinal absorption of the drug in certain patients. The present invention takes advantage of the discovery that taurocholic acid, or a pharmaceutically-acceptable salt thereof, when included with the novel, lactone-stable, "flipped" E-ring camptothecin in a solution dosage composition, results in improved absorption of the drug following ingestion of the composition. It is believed that this is due to the formation of a micellar solution of the novel, lactone-stable, "flipped" E-ring camptothecin on dilution thereof with the gastric contents.

The phenomenon of micellar solubilization of poorly water-soluble drugs mediated by bile acids, including taurocholic acid, has been previously reported with respect to glutethimide, hexesterol, griseofulvin (see, e.g., Bates, et al., Rates of Dissolution of Griseofulvin and Hexestrol in Bile Salt Solutions. Chem. Abstracts 65:8680b (1966); Bates, et al., Solubilizing Properties of Bile Salt Solutions on Glutethimide, Griseofulvin, and Hexestrol. Chem. Abstracts 64:9517e (1966); reserpine (see, e.g., Malone, et al., Desoxycholic Acid Enhancement of Orally Administered Reserpine. J. Pharmaceutical Sci. 55:972-974 (1966) and fatty acids and cholesterol (see, e.g., Westergaard, et al., The Mechanism Whereby Bile Acid Mycelles Increase the Rate of Fatty Acid and Cholesterol Uptake Into the Intestinal Mucosal Cell. J. Clinical Invest. 58:97-108 (1976). The use of taurocholic acid or a pharmaceutically-acceptable salt thereof in the present invention involves a pharmaceutical solution of the novel, lactone-stable, "flipped" E-ring camptothecin which has the unique property of providing a stable apparent solution of the drug upon dilution thereof with from 1 to 100 volumes of water. The solution is stable and free of precipitate for a period of at least two hours; sufficient time to permit administration and absorption by the patient.

It has been observed with similar solutions of etoposide, a different insoluble anti-cancer drug, that the bioavailability of the drug following oral administration is substantially equivalent to that achieved by intravenous administration of a solution of etoposide (U.S. Pat. No. 4,713,246). Analogous to that found with etoposide, it is believed that ingestion of the present dosage form of the novel, lactone-stable, "flipped" E-ring camptothecin and resulting dilution thereof by the stomach contents, results in the formation of a micellar solution of the novel, lactone-stable, "flipped" E-ring camptothecin in the stomach which is readily absorbed by the gastrointestinal tract. Applicants do not wish to be bound, however, by any theoretical explanation of the mechanism by which the superior oral bioavailability of the present the novel, lactone-stable, "flipped" E-ring camptothecin formulation is achieved.

Yet another embodiment of the present invention for oral administration to a patient with cancer said novel, lactone-stable, "flipped" E-ring camptothecin, pharmaceutically-acceptable salt, and/or an analog thereof, is dissolved in N-methylpyrrolidinone (NMP) in the presence of a pharmaceutically-acceptable acid, said novel, lactone-stable, "flipped" E-ring camptothecin, pharmaceutically-acceptable salt, and/or an analog thereof, is dissolved in dimethylisosorbide (DMI) in the presence of a pharmaceutically-acceptable acid, or said novel, lactone-stable, "flipped" E-ring camptothecin, pharmaceutically-acceptable salt, and/or an analog thereof, is dissolved in dimethylacetamide (DMA) in the presence of a pharmaceutically-acceptable acid.

A further embodiment of the present invention is the claimed composition and method of administering the composition by encapsulating the claimed formulations within a hard gelatin capsule. Still yet another embodiment of the claimed composition and method of administering the composition is encapsulating the claimed formulations within a soft gelatin capsule. One of ordinary skill in the art will know that any of the claimed formulations adapted for oral administration can be used as the fill for the soft or hard gelatin capsule.

Another embodiment of the present invention is an oral formulation of said novel, lactone-stable, "flipped" E-ring camptothecin, pharmaceutically-acceptable salt, and/or an analog thereof, in soft gelatin capsules (comprised of, for example, gelatin/glycerin/sorbitol/purifiers) containing 1.0 part of said novel, lactone-stable, "flipped" E-ring camptothecin, pharmaceutically-acceptable salt, and/or an analog thereof, in a vehicle comprising citric acid 0.1 to 0.9 parts by weight, glycerin 1 to 10 parts by weight, polyethylene glycol (molecular weight 200 to 300) 5 to 9 parts by weight, dehydrated ethyl alcohol 10 to 20% by weight of total solution weight, sodium acetate 0.05 to 0.5 parts by weight, a surfactant, and 1 to 10 parts dimethylisosorbide by weight. A more preferred oral formulation will include as a surfactant, pluronic F-127 poloxamer at 0.05 to 1.0 parts by weight.

Another preferred oral formulation will include the addition of taurocholic acid 2 to 10 parts by weight. The soft gelatine capsules may also be composed of any of a number of compounds used for this purpose including, but not limited to, a mixture of gelatine, glycerin, sorbitol, and parabens.

The present invention also provides for the formulation of the novel, lactone-stable, "flipped" E-ring camptothecin for rectal delivery and absorption via the utilization of rectal suppositories or retention enemas. Generally, suppositories are utilized for delivery of drugs to the rectum and sigmoid colon. The ideal suppository base for the delivery of the formulations of the present invention should meet the following specifications: (i) a base which is non-toxic and non-irritating to the anal mucous membranes; (ii) a base which is compatible with a variety of drugs; (iii) a bases with melts or dissolves in rectal fluids; and (iv) a base which is stable in storage and does not bind or otherwise interfere with the release and/or absorption of the pharmaceutical formulations contained therein. Typical suppository bases include: cocoa butter, glycerinated gelatine, hydrogenated vegetable oils, mixtures of polyethylene glycols of various molecular weights and fatty acid esters of polyethylene glycol. The rectal epithelium is lipoidal in character. The lower, middle, and upper hemorrhoidal veins surrounds the rectum. Only the upper vein conveys blood into the portal system, thus drugs absorbed into the lower and middle hemorrhoidal veins will bypass the liver and the cytochrome $P_{450}$ oxidase system. Absorption and distribution of a drug is therefore modified by its position within the rectum, in that at least a portion of the drug absorbed from the rectum may pass directly into the inferior vena cava, bypassing the liver. The present invention also provides for the formulation of novel, lactone-stable, "flipped" E-ring camptothecin, a pharmaceutically-acceptable salt thereof, and/or an analog thereof, as well as one or more chemotherapeutic agents, administered by suppository.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m² to approximately 100 mg/m² of said composition in single or divided dosages within a 24 hour period every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m² to approximately 75 mg/m² of said composition daily in single or divided doses for three consecutive days every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m² to approximately 50 mg/m² of said composition daily in single or divided doses for three consecutive days every 21 to 28 days.

Another embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m² to approximately 100 mg/m² of said composition in single or divided dosages within a 24 hour period given once per week for three consecutive weeks with 2 weeks rest after each 3 week cycle.

One embodiment discloses a method for the oral administration of a formulation comprising said novel, lactone-stable, "flipped" camptothecin, pharmaceutically-acceptable salt, and/or analog thereof, to a previously untreated patient with cancer, said method consisting of administering from approximately 0.1 mg/m² to approximately 75 mg/m² of said composition in single or divided doses within a 24 hour period once per week for three consecutive weeks with 2 weeks rest after each 3 week cycle.

Another embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m² to approximately 50 mg/m² of said composition in single or divided dosages within a 24 hour period given once per week for three consecutive weeks with 2 weeks rest after each 3 week cycle.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m²/day to approximately 100 mg/m²/day of said composition in single or divided daily doses administered within each 24 hour period for two to five consecutive days and repeated every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m²/day to approximately 75 mg/m²/day of said composition in single or divided daily doses administered within each 24 hour period for two to five consecutive days and repeated every 21 to 28 days.

One embodiment discloses a method for the oral administration of a formulation comprising said novel, lactone-stable, "flipped" camptothecin, pharmaceutically-acceptable salt, and/or analog thereof, to a patient with cancer, said method consisting of administering from approximately 0.1 mg/m²/day to approximately 50 mg/m²/day of said composition in single or divided daily doses administered within each 24 hour period for two to five consecutive days and repeated every 21 to 28 days.

Specific Examples of Formulations of the Present Invention

In its preferred embodiments, the present invention involves the preparation and administration of novel, lactone-stable, "flipped" E-ring camptothecin formulations. The following examples of the administration of these formulations illustrate selected modes for carrying out the present invention, and are not to be construed as limiting in any way.

Example I

For injection or infusion into aqueous body fluids, a formulation comprises a total dose of from approximately 0.1 mg/m$^2$ to approximately 100 mg/m$^2$ of the novel, lactone-stable, "flipped" E-ring camptothecin dissolved in 1 to 10 parts of N-methylpyrrolidinone, dimethylisosorbide and/or dimethylacetamide in an acidified vehicle comprising between approximately 10 to approximately 40 percent of an acceptable alcohol, approximately 4 to approximately 10 parts by weight of polyether glycol, and approximately 1 to approximately 10 parts of a non-ionic surfactant. Suitable alcohols include dehydrated ethyl alcohol, benzyl alcohol. Suitable polyether glycols, include polyethylene glycol 200, polyethylene glycol 300, propylene glycol. Suitable non-ionic surfactants include, but are not limited to, polysorbate-80. In a preferred embodiment, the formulation of the novel, lactone-stable, "flipped" E-ring camptothecin is supplied as an intravenous injectable in a 1 mg vial comprising a sterile, nonaqueous solution of drug in a vehicle comprising dehydrated ethyl alcohol, benzyl alcohol, citric acid, polyethylene glycol 300, and polysorbate (Tween 80) in acidified medium with a pH of 3 to 4 at a final concentration of 1 mg per 1 to 2 mL Example II A second formulation comprises a total dose of from approximately 0.1 mg/m$^2$ to approximately 100 mg/m$^2$ of the novel, lactone-stable, "flipped" E-ring camptothecin in an acidified vehicle comprising between approximately 0.1 to 2 parts of an alcohol and approximately 1 to 10 parts of a non-ionic surfactant. Suitable alcohols include dehydrated ethyl alcohol USP, and benzyl alcohol. Suitable non-ionic surfactants include the polyoxyethylated oils, such as polyoxyethylated vegetable oils, such as castor oil, peanut oil, and olive oil. In a preferred embodiment 1 mg to 200 mg the novel, lactone-stable, "flipped" E-ring camptothecin is formulated in 1 to 10 parts of N-methylpyrrolidinone, dimethylisosorbide and/or dimethylacetamide, 1 to 10 parts of Cremaphor EL™ (polyoxyethylated castor oil), 0.1 to 2 parts by weight dehydrated ethyl alcohol USP, and 0.1 to 0.9 parts citric acid to adjust the final pH between 3 to 4.

Example III

An oral formulation of the novel, lactone-stable, "flipped" "flipped" E-ring camptothecin in soft gelatin capsules (e.g., comprised of gelatin/glycerin/sorbitol/purifiers) containing 1.0 part of the novel, lactone-stable, "flipped" E-ring camptothecin in 1 to 10 parts of N-methylpyrrolidinone, dimethylisosorbide and/or dimethylacetamide, citric acid 0.1 to 0.5 parts by weight, glycerin 1 to 10 parts by weight, and polyethylene glycol 200 to 300 5 to 9 parts by weight, dehydrated ethyl alcohol 0.2 to 2 parts by weight of total solution weight, sodium acetate 0.05 to 0.5 parts by weight, pluronic poloxamer using 0.05 to 1.0 parts by weight, and taurocholic acid 2 to 10 parts by weight. The soft gelatin capsules may also be composed of any of a number of compounds used for this purpose including, for example, a mixture of gelatin, glycerin, sorbitol, and parabens.

It should be noted that in order to prolong the stability and solubility of the novel, lactone-stable, "flipped" E-ring camptothecin for clinical infusions, the drug may diluted in 5% Dextrose in water (D5W) to a final concentration so as to provide a total dose of approximately 0.1 mg/m$^2$ to approximately 100 mg/m$^2$ of the novel, lactone-stable, "flipped" E-ring camptothecin prior to injection or infusion.

Maintaining an acidic pH (i.e., pH 3 to 4) in the formulation is particularly important to reduce the slow conversion of the novel, lactone-stable, "flipped" E-ring camptothecin (i.e., active form) to the E-ring-hydrolyzed carboxylate (i.e., inactive form), which occurs at physiological pH. At equilibrium under physiologic pH, the ratio of the inactive, "open-ring" form to lactone increases. Hence, hydrolysis of the lactone ring will be substantially reduced if the drug is kept in an acidic environment. The lactone form of, e.g., naturally-occurring camptothecin, as in the novel, lactone-stable, "flipped" E-ring camptothecin of the present invention, is less water soluble than the carboxylate E-ring form. As previously discussed, when early clinical trials were first conducted with camptothecin using NaOH, the significance of maintaining the closed lactone ring for uniform efficacy in treating patients with cancer was poorly understood. The early reported unpredictable clinical toxicities associated with camptothecin administration may have been exacerbated by the NaOH formulation which promotes the formation of the carboxylate form, and by the relative lack of understanding of the significance of the lactone form of camptothecin as it relates to chemotherapeutic activity.

Specific Examples of the Administration of Formulations

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

The administration of the novel, lactone-stable, "flipped" E-ring camptothecin of the present invention may be carried out using various schedules and dosages. For example:

(1) For intravenous administration, a suitable dose is approximately 0.1 mg/m$^2$ to approximately 100 mg/m$^2$ in a 24 hour period which can be administered in a single or divided into multiple doses, depending upon the attending physician. This dosing regiment may be repeated for 48 hours or more. Other suitable intravenous dosing schedules range from approximately 0.1 mg/m$^2$ to approximately 100 mg/m$^2$ per day using a 3 to 5 day continuous infusion schedule every 21 to 30 days and approximately 0.1 mg/m$^2$ to approximately 100 mg/m$^2$ given as a 30 to 90 minute infusion every 21 to 30 days.

(2) A suitable oral dose of the drug is approximately 0.1 mg/m$^2$ to approximately 100 mg/m$^2$ per day using the lower dose for a period of 3 to 5 days and using divided dosages of administration of two to four times per day. Other suitable oral dosing schedules range from approximately 0.1 mg/m$^2$ to approximately 75 mg/m$^2$ per day for a period of 3 to 5 days and approximately 0.1 mg/m$^2$ to approximately 50 mg/m$^2$ per day for a period of 3 to 5 days.

It should be noted that the parenteral and oral doses can be administered under the supervision of a physician based on gradual escalation of the dosage to achieve the maximum tolerated dose in the individual patient. The oral administration schedule of the novel, lactone-stable, "flipped" E-ring camptothecin may involve multiple daily doses or single daily doses for one or more consecutive days with the ability of the physician to optimize therapy by reaching the maximum effective chemotherapeutic dose that has the least toxicity in the individual patient.

In addition, patients may be given the novel, lactone-stable, "flipped" E-ring camptothecin of the present invention as either an inpatient or outpatient, using the following exemplary schedules:

(1) approximately 0.1 mg/m$^2$ to approximately 100 mg/m$^2$ given over 90 minutes I.V. every 21 to 28 days;

(2) approximately 0.1 mg/m$^2$ to approximately 100 mg/m$^2$ given daily for three consecutive days over 90 minutes I.V. every 21 to 28 days;

(3) approximately 0.1 mg/m$^2$ to approximately 100 mg/m$^2$ week given once per week X 3 consecutive weeks over 90 minutes I.V. with 2 weeks rest after each 3 week cycle for pretreated patients;

(4) approximately 0.1 mg/m$^2$ to approximately 100 mg/m$^2$ given once per week X 3 consecutive weeks over 90 minutes I.V. for previously untreated patients with 2 weeks rest after each 3 week cycle; and (5) approximately 0.1 mg/m$^2$/d to approximately 100 mg/m$^2$/d X 3-5 consecutive days as a continuous i.v. infusion every 21 to 28 days.

In a preferred embodiment, the novel, lactone-stable, "flipped" E-ring camptothecin is initially given at a lower dose. The dose of the novel, lactone-stable, "flipped" E-ring camptothecin is then escalated at each successive cycle of treatment until the patient develops side effects which demonstrates individual therapeutic tolerance. The purpose of dose escalation is to safely increases the drug levels to a maximum tolerated dose and should result in increased cytotoxicity and improved chemotherapeutic activity.

Dosages can be escalated based on patient tolerance as long as unacceptable toxicity is not observed. "Unacceptable toxicity" is defined by World Health Organization (WHO) as grade 3 non-hematologic toxicity excluding nausea and vomiting and grade 4 vomiting or hematologic toxicity according to the National Cancer Institute common toxicity criteria. Since some clinical drug toxicity is anticipated in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

Determination of Serum Levels

Kaneda's HPLC method and further modifications by Barilero, et al., (Simultaneous Determination of the Camptothecin Analogue CPT-11 and Its Active Metabolite HECPT by High Performance Liquid Chromatography: Application to Plasma Pharmacokinetic Studies in Cancer Patients. *J. Chromat.* 575:275-280 (1992)) are useful for the measuring quantities of various camptothecins (including the novel, lactone-stable, "flipped" E-ring camptothecin of the present invention) in plasma and tissue.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A lactone-stable, "flipped" E-ring camptothecin analog consisting of the structure illustrated below:

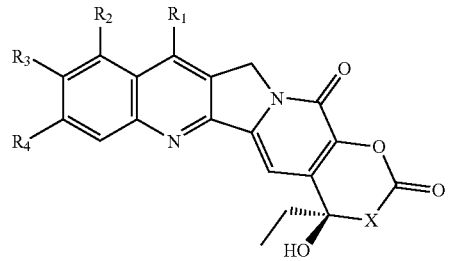

wherein;

X is —$(CH_2)_n$—; wherein $n \leq 2$ or $CF_2$;

$R_1$ is —$(CH_2)_n$—, —$(CH_2)_n Si(R_5)_3$, —$(CH_2)_n Ge(R_5)_3$; wherein n=0 to 6; any halide; any short chain amine; and wherein $R_5$ is $CH_3$, $C_2H_5$, $C_3H_8$;

$R_2$ is —$(CH_2)_n$—, —$(CH_2)_n Si(R_5)_3$, —$(CH_2)_n Ge(R_5)_3$; wherein n=0 to 6; any halide; any short chain amine; and wherein $R_5$ is $CH_3$, $C_2H_5$, $C_3H_8$;

$R_3$ and $R_4$ are any halide; any short chain amine; $CH_3O$; —$OCH_2CH_2O$—, —$OCH_2O$—; or a pharmaceutically-acceptable salt thereof.

2. The lactone-stable, "flipped" E-ring camptothecin analog of claim 1, wherein $R_1$ is selected from the group consisting of: —X-(lower alkyl)-Si(alkyl)$_3$ or —X-(lower alkyl)-Ge (alkyl)$_3$.

3. The lactone-stable, "flipped" E-ring camptothecin analog of claim 1, wherein $R_1$ is selected from the group consisting of: a -(lower alkyl)-Si moiety or a -(lower alkyl)-Ge moiety; and wherein one or two of $R_2$ through $R_4$ is a moiety selected from the group consisting of: amino, substituted amino, hydroxy, alkoxy, -carbonyl-lower alkyl-heterocycle, -lower alkyl-trimethylsilyl, -lower alkyl-trimethylgermanium or aryloxy.

* * * * *